(12) United States Patent
Allen-Hoffmann et al.

(10) Patent No.: US 6,884,595 B2
(45) Date of Patent: *Apr. 26, 2005

(54) IMMORTALIZED HUMAN KERATINOCYTE CELL LINE

(75) Inventors: B. Lynn Allen-Hoffmann, Madison, WI (US); Sandra J. Schlosser, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/299,938

(22) Filed: Nov. 19, 2002

(65) Prior Publication Data

US 2003/0157476 A1 Aug. 21, 2003
US 2004/0265787 A9 Aug. 21, 2003

Related U.S. Application Data

(63) Continuation of application No. 09/789,124, filed on Jan. 24, 2001, now Pat. No. 6,485,724, which is a continuation of application No. 09/277,295, filed on Mar. 26, 1999, now Pat. No. 6,214,567, which is a continuation of application No. 09/114,557, filed on Jul. 13, 1998, now Pat. No. 5,989,837.

(51) Int. Cl.[7] .................. G01N 33/567; C12Q 1/02; C12N 5/08
(52) U.S. Cl. ................ 435/7.21; 435/29; 435/371
(58) Field of Search ............ 435/7.21, 347, 435/371, 373, 402, 408, 29

(56) References Cited

U.S. PATENT DOCUMENTS

| | | | |
|---|---|---|---|
| 5,491,084 A | | 2/1996 | Chalfie et al. |
| 5,989,837 A | * | 11/1999 | Allen-Hoffmann et al. ...... 435/7.21 |
| 6,214,567 B1 | * | 4/2001 | Allen-Hoffmann et al. ...... 435/7.21 |
| 6,514,711 B1 | * | 2/2003 | Allen-Hoffmann .......... 435/7.21 |

OTHER PUBLICATIONS

L. Allen–Hoffmann, et al., Proc. Nat'l Acad. Sci. USA 81:7802–7806, 1984.

B.L. Allen–Hoffmann, et al., "Use of RHEK–1 Immortalized Human Keratinocytes for Detection of Induced Mutation at the Hypoxanthine–guanine Phosphoriboxyltransferase Locus," Inter. J. Oncol. 3:619–625 1993.

H.P. Baden, et al., "Isolation and Characterization of a Spontaneously Arising Long–lived Line of Human Keratinocytes (NM1)," In Vitro Cell Dev. Biol. 23(3):205–213, 1987.

P. Boukamp, et al., "Cell Keratinization in a Spontaneously Immortalized Diploid Human Keratinocyte Cell Line," J. Cell Biol. 106:761–771, 1988.

P. Boukamp, et al., "Normal Keratinization in a Spontaneously Immortalized Aneuploid Human Keratinocyte Cell Line," J. Cell Biol. 106:761–771, 1988.

J.A. Garlick and L.B. Tachman, "Fate of Human Keratinocytes during Reepithelization in an Organotypic Culture Model," Lab. Invest. 70(6):916–924, 1994.

J.A. Garlick, et al., "Re–epithelialization of Human Oral Keratinocytes In Vitro," J. Dent. Res. 75(3):912–918, 1996.

J.A. Garlick, et al., "Skin Substitutes–Tissue Models for Cancer Biology," Bioengineering of Skin Substitutes, Sep. 18–19, Boston, MA, 1997.

C. Gilles, et al. "Immortalization of Human Cervical Keratinocytes by Human Papillomavirus Type 33," Int. J. Cancer 53:872–879, 1993.

M.A. Pickart, et al., "Development of an Organotypic Culture System for the Study of Human Squamous Cell Carcinoma," Proc. Am. Assoc. Canc. Res. 40:192, 1999 (Abstract).

R.H. Rice, et al., "Elevation of Cell Cycle Control Proteins During Spontaneous Immortalization of Human Keratinocytes," Mol. Biol. Cell 4:185–194, 1993.

D. Strickland, "Organogenesis gets Approval from FDA from Graftpatch: Stock Jumps 7 Percent," Bioworld Today 8(154):1–4, 1997.

* cited by examiner

Primary Examiner—Mary E. Mosher
(74) Attorney, Agent, or Firm—Quarles & Brady LLP

(57) ABSTRACT

A spontaneously immortalized human keratinocyte cell line is disclosed. In a preferred embodiment, this cell line is ATCC 12191. In another embodiment of the invention, a method of assaying the effect of a test tumor cell modulation agent is disclosed. The method comprises the steps of obtaining a human stratified squamous epithelial cell culture, wherein the culture comprises human malignant squamous epithelial cells and spontaneously immortalized human keratinocytes, wherein the culture forms a reconstituted epidermis. One then treats the epidermis with a test tumor cell modulation agent and evaluates the growth of the malignant cells within the epidermis.

21 Claims, 4 Drawing Sheets

FIG. 6A
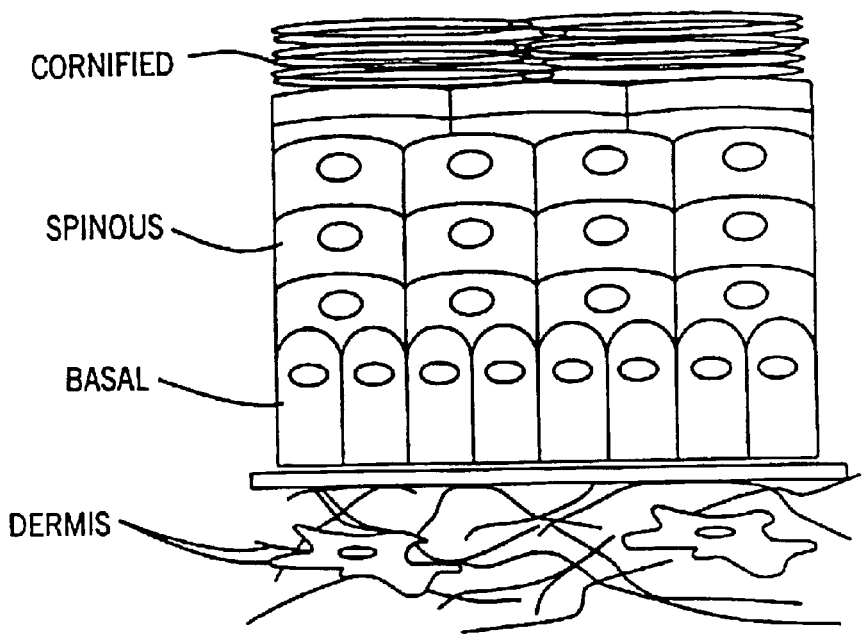
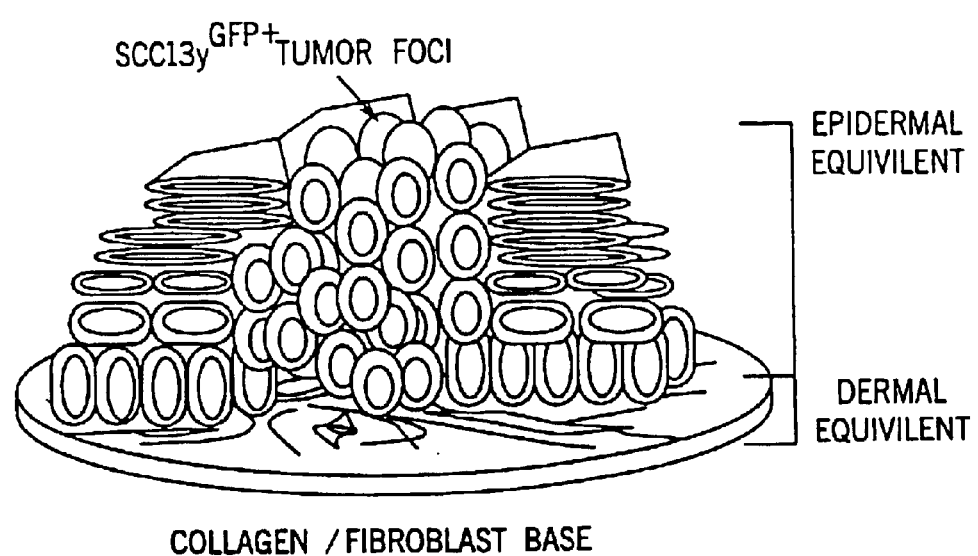
FIG. 6B

IMMORTALIZED HUMAN KERATINOCYTE CELL LINE

This application claims priority to and is a continuation of Ser. No. 09/769,124, filed Jan. 24, 2001, and issued as U.S. Pat. No. 6,485,724, which is a continuation of Ser. No. 09/277,295, filed Mar. 26, 1999, issued as U.S. Pat. No. 6,214,567, which was a continuation of Ser. No. 09/114,557, filed Jul. 13, 1998, issued as U.S. Pat. No. 5,989,837.

STATEMENT REGARDING FEDERALLY SPONSORED RESEARCH OR DEVELOPMENT

This invention was made with United States government support awarded by the following agency: NIH Grant No. AR40284. The United States has certain rights in this invention.

CROSS-REFERENCE TO RELATED APPLICATION

Not applicable.

BACKGROUND OF THE INVENTION

Human Keratinocytes

Human keratinocytes isolated from stratified squamous epithelia can be readily cultivated in vitro (reviewed in Leigh, et al., 1994). Cultivated keratinocytes replicate readily during early passage and can generate large numbers of cells which exhibit certain features of squamous differentiation in vivo. When cultured normal human keratinocytes are transplanted onto mice, epidermal tissue architecture is regenerated over time in an orderly fashion (Breitkreutz, et al., 1997). The ease of cultivation and transplantation of human keratinocytes coupled with the accessibility of skin for the grafting procedure and subsequent monitoring, make this somatic cell type attractive for therapeutic gene delivery. However, due to the initiation of terminal differentiation, transgene expression in keratinocytes is consistently lost regardless of the gene expression strategy used. Several reports have shown that genetically engineered human keratinocytes can recapitulate full thickness epidermis, thus demonstrating that cells with stem cell-like properties were present in the transplanted population of cells (Choate and Khavari, 1997; Choate, et al., 1996; Gerrard, et al., 1993; Garlick, et al., 1991; Greenhalgh, et al., 1994; Vogel, 1993, Fenjves, 1994).

In Vitro Tissue Culture Assays Utilizing Human Cells Derived from Stratified Squamous Epithelia In vitro assays using monolayer cultures of adherent cells which maintain the normal in vivo tissue context do not exist for human tissues. Animal models do have the capacity to mimic some of the processes involved in the response of human tissue therapies. However, animal systems lend themselves only to qualitative and subjective scoring of tumor repopulation. Historically, simple in vitro growth assays have used monolayer cultures of rodent or human cell lines on plastic tissue culture dishes. Colony size or cell number are assessed in order to estimate the extent of survival and repopulation of cancer cells following radiation treatment. A manor drawback of this approach is that it does not account for any adhesive or paracrine growth factor signals within the tumor cell environment. For this reason, studies on the growth of tumor cells in the absence of normal surrounding tissue may not accurately reflect the in vivo growth characteristics of tumor cells.

For example, human head and neck (H&N) tumors are diagnosed in 43,000 patients in the United States every year and in over 750,000 patients worldwide. Although tumor recurrence near the site of the primary tumor is the predominant cause of treatment failure and death for these patients, little is know about the molecular events contributing to tumor regrowth following treatment. Clinical and radiobiological evidence suggests that tumor proliferation rates may actually increase following wounding due to radiation exposure (Hall, E. J., 1988; Petereit, D. G., et al., 1995). It has been suggested that the wound environment provides potent tumor growth signals (Haddow, A., 1972). For example, extracellular matrix (ECM) glycoproteins present in the wound bed provide and/or sequester potent growth stimuli required for normal tissue regeneration. It is clear from these observations that the tissue context in which a tumor initially develops and/or regrows following failed cancer treatment may have significant impact on tumor growth.

Needed in the art of cell biology is a spontaneously immortalized human keratinocyte cell line with near normal chromosomal complement and a method for using this immortalized cell line in an in vitro tissue assay.

SUMMARY OF THE INVENTION

In one embodiment, the present invention is an immortalized human keratinocyte cell line, wherein the cell line comprises a normal chromosomal complement of 46 with the exception of an extra isochromosome on the long arm of chromosome 8. In one particularly advantageous embodiment, the cell line is ATCC CRL 12191.

In another embodiment, the present invention is a transgenic immortalized human keratinocyte cell line transfected with a heterologous gene. This gene may be a marker gene, most preferably green fluorescent protein (GFP).

The present invention is also a method of assaying the effect of a test tumor cell therapeutic agent by obtaining a human stratified squamous epithelial cell culture comprising malignant squamous epithelial cells, preferably human squamous carcinoma cells (SCC), and spontaneously immortalized human keratinocytes. This culture is then formed into a reconstructed epidermis. One may then treat the epidermis with a test tumor cell therapeutic agent and evaluate the growth of the SCC within the epidermis.

It is an advantage of the present invention that an immortalized keratinocyte cell line is provided.

Other objects, features and advantages of the present invention will become apparent after review of the specification, claims and drawings.

BRIEF DESCRIPTION OF THE SEVERAL VIEWS OF THE DRAWINGS

FIG. 6 is a cross-sectional schematic of skin and organotypic $SCC13y^{GFP+}$/BC-1-Ep/SL culture. FIG. 6A is a schematic of the multiple layers present in skin. FIG. 6B is a schematic of a tumor/normal tissue model consisting primarily of three components as shown. The base layer is a dermal-equivalent consisting of collagen and fibroblasts. Above this layer, is the reconstructed epidermis formed by differentiating BC1-Ep/SL epithelial cells (shaded). Within this epidermal equivalent is an SCC13 $y^{GFP+}$ tumor foci (not shaded).

BRIEF DESCRIPTION OF THE INVENTION

A. Immortalized Human Keratinocyte Cell Line

Figure 1:
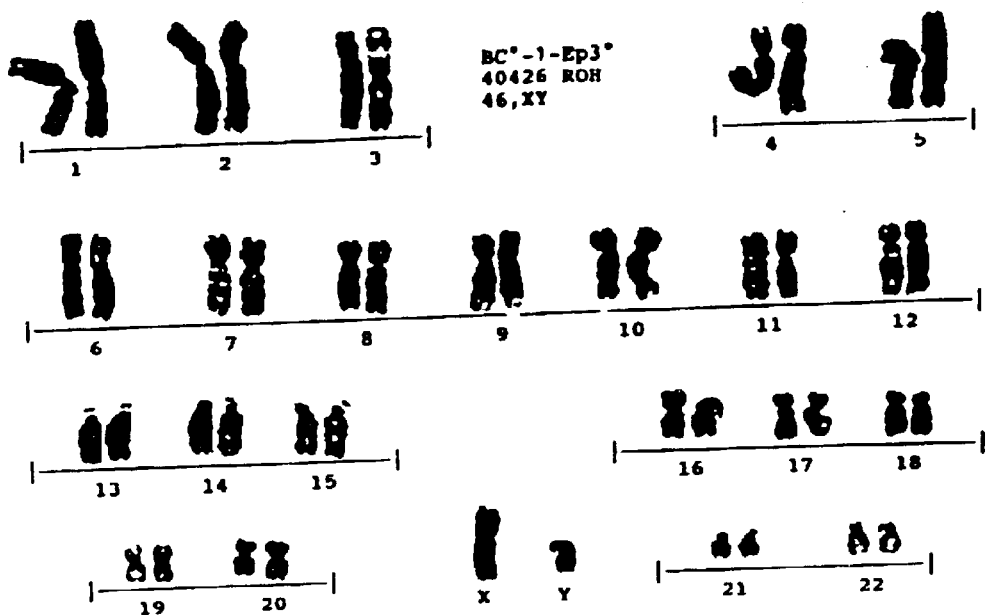
FIG. 1 is a chromosomal analysis of BC-1-Ep/SL cells. Karyotypic analysis was performed on BC-1-Ep/SL cells at passage 31. The cells contained 47 chromosomes due to an extra isochromosome of the long arm of chromosome 8. The extra chromosome, i(8q), is not seen in the parental keratinocytes (BC-1-Ep passage 3) which exhibited a normal male karyotype.
Figure 1:
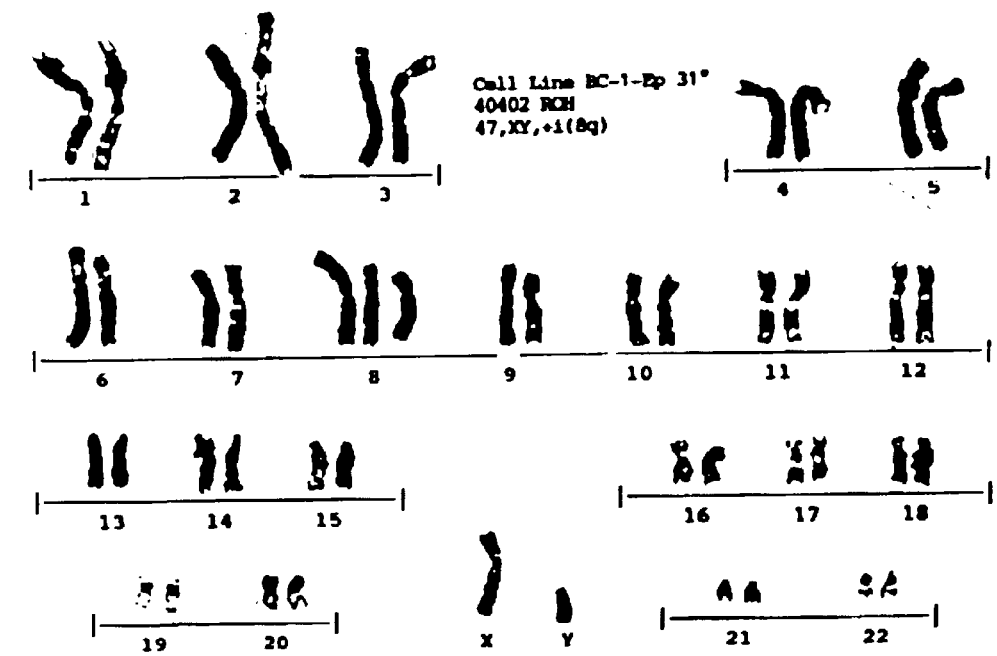

Human keratinocytes with stem cell-like properties are the optimal target for stable transfection of exogenous genes. Stable transfectants are produced when exogenous DNA is introduced into a cell and integrates into the host chromosomes. Subsequent daughter cells express the gene product of the transgene and are stable if the expression is propagated indefinitely throughout subsequent generations. For gene therapy applications, it is essential to use stem cell-like keratinocytes with the ability to regenerate full thickness epidermis for multiple cycles of tissue turnover while maintaining expression of the transduced gene of interest.

In one embodiment, the present invention is a spontaneously immortalized human keratinocyte cell line, BC-1-Ep/SL, which maintains cell type-specific growth requirements, expresses differentiation markers, and can be stably transfected. BC-1-Ep/SL was deposited on Sep. 20, 1996 with the American Type Culture Collection at 10801, University Boulevard, Manassas, Va. 20110-2209, USA, under Accession No. CRL-12191 under the terms and conditions of the Budapest Treaty.

BC-1-Ep/SL keratinocytes are not tumorigenic and undergo squamous differentiation in organotypic culture. Organotypic cultures are cultures in which keratinocytes are grown on a substrate that resembles the dermis and are exposed to the air-medium interface (Leigh ant Watt 1994).

We envision that this human keratinocyte cell line will serve as a source of long-lived epidermal progenitor cells capable of supporting high efficiency and long-term epidermal transgene expression. BC-1-Ep/SL keratinocytes represent an important new cellular reagent for the study of growth and differentiation in stratified squamous epithelia.

In another embodiment, the present invention is a immortalized human keratinocyte cell line, preferably BC-1-Ep/SL, preferably ATCC CRL-12191, comprises at least one transgene. The Examples below demonstrate a preferred method of creating a transgenic cell line. Many other methods would be apparent to one of skill in the art of molecular biology. We have developed a method whereby the transfected BC-1-Ep/SL keratinocytes are identified based on the expression of GFP and are selected based on morphology and degree of GFP expression, and as such preserve the highest degree of the cells pre-transfection, natural state/qualities. This technique avoids the potential character-altering pressures due to selection based on a dominant selectable marker with standard chemical agents such as F418, methotrexate, hygromycin-B, aminopterin, mycophenolic acid, and zeocyn.

We envision that one would wish to use the immortalized human keratinocyte cell line in a variety of ways such as formation of an organotypic culture, with monolayer cell culture, a human tissue-engineered product appropriate for short- and/or long-term grafting to humans or research animals, and as a biofilm component, e.g., as part of a machine which produces gene products to continually be administered to a patient intravenously.

B. Use of BC-1-Ep/SL as a Model Organotypic System

As described above, the cell line of the present invention has the substantial advantage of reproducing the tissue architecture of normal human stratified squamous epithelia. This model is suitable as an assay of human tumor repopulation. By entirely reconstructing malignant human epithelial cell growth within a tissue-like environment, tumor cell growth characteristics can be monitored in a physiologically relevant context.

In addition, quantitative endpoints can be monitored because each individual tumor cell could be genetically engineered to express a marker protein, such as green fluorescent protein (GFP). (The Examples below demonstrate a preferred method of transfecting BC-1-Ep/SL with a marker gene.) This model system represents a technological advancement for the screening of drugs or agents used in the treatment of cancers of stratified squamous epithelia. Illustrative cancers include cancers of the head and neck, skin, oral mucosa, cervix, and trachea.

Therefore the present invention is a human stratified squamous epithelial model system designed to measure the rate of tumor cell growth and repopulation (see FIG. 6 in Examples for schematic).

In one embodiment, the model system consists of an organotypic co-culture of genetically marked human squamous cell carcinoma (SCC) cells and unmarked spontaneously immortalized human keratinocytes, BC-1EP/SL. The BC-1-EP/SL keratinocyte line is a critical component in the model system because the cells provide a reproducible environment context in which to compare the growth characteristics of SCC cells. The BC-1-EP/SL immortalized cell line is highly advantageous because it maintains all the characteristics of a normal keratinocyte, i.e., terminal differentiation, apoptosis, and non-tumorigenic characteristics remain.

The Examples below disclose a preferred method of creating a reconstructed epidermis. In brief, BC-1-EP/SL and SCC cells are seeded onto a base of collagen containing normal human fibroblasts. The co-culture is seeded at various dilutions of marked SCCs in a standard number of BC-1-EP/SL keratinocytes.

The in vitro tumor/normal tissue model of the present invention will also aid in experimentation of the molecular mechanisms responsible for tumor progression and repopulation. This same model may also be used to identify potential cytostatic agents which can slow tumor regrowth and chemopreventive agents with specific tumor selectivity. For example, the reconstituted organotypic cultures can be treated with a variety of tumor cell modulation agents, such as physical (e.g., x-irradiation) or chemical/biological agents (i.e., chemotherapeutic agents, cytostatic drugs), and the cultures monitored, preferably using the GFP labelling, to quantify the extent or lack of SCC cell (re)growth. In this way, the BC-1-EP/SL model system will contribute to the identification and development of antiproliferative agents for cancer patients receiving curative therapies for cancers of the head and neck, skin, oral mucosa, cervix, trachea, and other epithelia or novel, new anticancer strategies, in general.

Tumor cell growth may be most conveniently monitored in the following manner: The total number of tumor cells and ratio to the number of BC-1-Ep/SL cells can be most conveniently monitored using flow cytometry techniques based on GFP fluorescence. Tumor cell volume and localization is most conveniently monitored by confocal microscopy. Cell-cell interactions are most conveniently monitored in histologic sections using immunostaining and in situ hybridization techniques.

Introduction of GFP into mammalian cells is increasingly utilized for in vitro and animal model systems. To date, there are no reports describing altered mammalian cell growth characteristics due to GFP expression. The fact that these models behave as expected suggests that GFP expression is innocuous and thus an ideal marker protein. Observations in this study have also confirmed that introduction of GFP into the human squamous cell carcinoma cell line, SCC13y, has no effect on relevant biologic endpoints. The results observed in these experiments support previous studies which suggest GFP expression does not interfere with growth and differentiation characteristics of the cell types studied. Stability of GFP expression is another variable which is critical to the success of models which utilized GFP as a marker over time. Our experimental observations suggest that GFP expression is stable in at least one malignant cell line, SCC13y. Other methods of genetic marking, e.g., enzymatic activity and/or culture devices are being considered to allow repeated assay of the same culture sample.

The co-culture of abnormal and normal human keratinocytes has recently been reported by A. Javaherian and co-workers (Javaherian, A., et al., 1998). In this study, keratinocyte cells (HaCat) which have been immortalized using genetic engineering are grown in organotypic culture. Though immortal, these cells are not tumorigenic, i.e., able to form malignant tumors in nude mice, and thus are not representative of malignant cells in general. Since the SCC13y$^{GFP+}$ cell line is derived from an actual patient tumor and is tumorigenic, it may be more appropriate for studies aimed at eradication of malignant tumors.

The organotypic co-culture model may be useful for at least three critical problems faced by the pharmaceutical and biotechnology industries: (1) how to screen for novel cytostatic inhibitors of tumor repopulation, (2) how to determine patient-specific responses to chemotherapy or radiotherapy prior to treatment, and (3) how to develop novel, biologic therapeutic agents. Unlike traditional cytotoxic agents which target the tumor cell directly, cytostatic inhibitors of tumor growth may target the individual tumor or its microenvironment. This difference arises predominantly because the primary aim of a cytotoxic agent is to kill the tumor cell; whereas, cytostatic agents aim to slow or halt tumor proliferative expansion but do not necessarily kill it. In theory, this can be achieved by direct interference with cellular proliferation (e.g., cell cycle inhibitors) or by indirect alterations in the surrounding normal tissue which make it less supportive of tumor growth (e.g., inhibition of wound regenerative signals).

Novel antitumor strategies may be identified using organotypic tumor/normal tissue co-culture because in vitro function of tumor and normal tissue responses can be assayed directly in reconstructed human tissues. Current in vitro assays based on the growth of monolayer cultures of human tumor cells fail in this regard because they do not require normal tissue function nor do they account for the influence of the microenvironment of the malignant cells. Understanding the tumor microenvironment may be of particular importance an identification of chemopreventive agents which focus on preventing the initiation of a tumor when it has yet to develop aggressive malignant characteristics. It may also be important for prevention of regrowth of malignant cells which survive conventional cytotoxic or surgical therapies. Additionally, cytostatic agents with organotypic tumor/normal tissue co-culture, may also be useful for concurrent use for clinical radiotherapy. In this case, the capacity of cytostatic agents to slow the tumor growth during treatment may be critical in eliminating the tumor and may attenuate the complications produced by inflammation which accompanies conventional therapies.

Monitoring tumor regrowth in an organotypic tumor/ normal tissue co-culture model may also be useful for providing pretreatment patient-specific information regarding therapy responsiveness and therapeutic ratio. Current assays have demonstrated only a weak correlation between in vitro growth of human tumors in monolayer culture and actual patient tumor response. Stronger correlations could be achieved by including the normal tissue context within in vitro models.

Other applications may provide additional prognostic and/or biologic materials with potential to directly impact patient treatment. For instance, cells from tumor biopsies could be co-cultured with GFP-labelled BC-1-EP/SL cells, defined herein as "inverse culture." An inverse culture model would provide a reproducible culturing environment which closely mimics the in situ tumor microenvironment and would allow assays of individual patient's tumor cells. Specific treatments could then be tested with the biopsied tumor sample in culture before actual patient treatment commences. In this way, treatments may be individually tailored to each patient based on test responses.

An important property of an organotypic tumor/normal tissue "inverse" co-culture model is that it may closely mimic the tumor microenvironment specific to that patient. This may be highly advantageous for development of some novel forms of biologic treatment such as immune therapy. The goal of immune therapy is to prime the patients own immune effector cells, e.g., B cells, helper T cells, cytolytic T cells (CTLs), or natural killer cells (NK) in vitro, and then return these activated cells to the patient in order to target and eradicate the tumor. Current in vitro cultures may not be as efficient as organotypic cultures for the priming of immune effector cells. A potential reason for lack of activation of the immune effector cells is inefficient and/or unsuccessful presentation of the appropriate tumor specific antigens (TSAs). An organotypic tumor/normal tissue "inverse" co-culture model may eliminate this problem. Because it accurately reconstructs the in situ tumor microenvironment, TSAs may be more likely to be expressed in organotypic culture; and, thus, may have a higher chance of being presented to the immune effector cells.

B. Other Embodiments

1. Use as a universal donor epidermal cell type in living tissue products for the repair and/or support of appropriate epithelial tissues. An example of an application is venous leg ulcers, which affect about 1 million people in the United States and 3 million worldwide, and other ulcer conditions such as diabetic ulcers and pressure ulcers (bedsores), which affect approximately 10 million people worldwide. The BC-1-Ep/SL keratinocyte cell line could also be used in a wide range of clinical applications, for example, acute burn coverage, dermatological surgery wounds, donor site wounds (for coverage after skin is harvested to be used elsewhere).

2. Use includes the development and testing of agents used in the formulation of therapeutic, cosmeceutical, and cosmetic skin products applied in cream, lotion, liquid, and spray forms. The cells provide a consistent source of human keratinocytes to test toxicity, potency, and efficacy of such agents. Cells could be used in monolayer culture for these assays or in the organotypic cultures. Organotypic cultures could be used to develop and assay effects of agents on tissue architecture, differentiation, cell replication and growth, barrier function, and tissue strength.

3. Use includes recipient cell for the cultivation of biological agents, such as human papilloma viruses, so that vaccines against viruses can be produced. The cell line could also be used to develop and test antiviral drugs and agents. Over 60 different types of human papilloma viruses produce warts in humans, including genital warts and viral lesions that are tightly associated with the development of cervical cancer in women and penile cancer in men. Human papillomaviruses are small double-stranded DNA viruses which are widespread in the human population. They are strictly epitheliotropic and infect only cutaneous and mucosal skin from a range of anatomic sites. Human papillomaviruses replicate only in human epithelial cells which are undergoing differentiation.

EXAMPLES

1. Normal Growth and Differentiation in a Spontaneously Immortalized Near-Diploid Human Keratinocyte Cell Line, BC-1-Ep/SL A. Materials and Methods Cell Culture Normal keratinocytes (BC-1-Ep) were isolated from newborn human foreskin. Keratinocyte cultures were established by plating aliquots of a single cell suspension in the presence of mitomycin C-treated Swiss mouse 3T3 fibroblasts as described by Allen-Hoffmann and Rheinwald (1984). The standard keratinocyte culture medium was composed of a mixture of Ham's F12:Dulbecco's modified Eagle's medium (DME), (3:1, 0.66 mM calcium, supplemented with 2.5% fetal calf serum (FCS), 0.4 µg/ml hydrocortisone (HC), 8.4 ng/ml cholera toxin (CT), 5 µg/ml insulin (Ins), 24 µg/ml adenine (Ade), 10 ng/ml epidermal growth factor (EGF), 100 units penicillin and 100 µg/ml streptomycin (P/S). The cells were passaged at weekly intervals at $3 \times 10^5$ cells on a 100 mm² tissue culture dish with feeders. Transformed cells, BC-1-Ep/SL (spontaneous line), appeared at passage 16. BC-1-Ep/SL cells at passage 55 tested negative for mycoplasma (Wisconsin State Laboratory of Hygiene, Madison, Wis.). Recombinant human EGF obtained from R+D Systems. Transforming growth factor beta (TGF-(1) was purified from human platelets.

Chromosomal Analysis

Cells in log phase growth were arrested in metaphase with 50 ng/ml colcemid, then trypsinized and pipetted from the flask for centrifugation. After removal of the media and trypsin, the cells were suspended in a hypotonic 75 mM KCl solution for 20 minutes, fixed with 3:1 methanol/acetic acid three times and dropped onto glass slides. Slides were aged two weeks, lightly trypsinized and stained with Giemsa (Seabright, 1971). In each sample, the chromosomal identities and abberations were determined in well-spread G-banded metaphases by photographic analysis and the cutting of at least two karyotypes for band to band comparison of chromosomal homologs.

DNA Fingerprinting

DNA was isolated from keratinocytes using Qiagen QIAamp Blood Kit (Qiagen, Inc., Santa Clarita, Calif.). DNA fingerprint analysis used the GenePrint (Fluorescent STR System according to protocols recommended by manufacturer. The twelve primer pairs are divided into three quadriplexes (CTTv, FFFL, and GammaSTR). Each quadriplex was amplified in separate reactions using 25 ng of DNA as template. Amplification was preformed in a Perkin-Elmer 9700 thermal cycler (Perkin-Elmer, Corp., Norwalk, Conn.). PCR products were electrophoresed on 42 cm×33 cm×0.4 mm polyacrylamide gels in a BRL sequencing apparatus (Life Technologies, Inc., Gaithersburg, Md.). Gels were then scanned on a Hitachi FMBIO(II Fluorescent Scanner.

Growth of BC-1-Ep/SL Cells in Athymic Mice

BC-1-Ep/SL cells were injected into nude athymic mice to determine if they could form tumors. A suspension of $5 \times 10^6$ cells in 100 µl Ham's F12 was infected subcutaneously into the flanks of six nude mice. As a negative control, the parental BC-1-Ep 6(cells were injected at $3 \times 10^6$ cells/100 µl F12. As a positive control, SCC4 cells were injected at $3 \times 10^6$/100 µl F12. Mice were weighed and tumors measured 26 days later.

Suspension in Semi-solid Media

For suspension studies, preconfluent cultures were removed from culture dishes with 0.5 mM EDTA, 0.1% trypsin and washed in serum-containing medium to inactivate any residual trypsin. After a short centrifugation (440×g for 3 minutes), cells were resuspended at $1 \times 10^6$ cells/ml in 3 parts Ham's F-12 plus 1 part DME made semi-solid with 1.68% methylcellulose (4,000 centipoises, Fisher Scientific, Fairlawn, N.J.) as described in Sadek and Allen-Hoffmann, 1994 (Sadek, C. M. and B. L. Allen-Hoffmann, 1994). Cells were recovered from suspension by repeated dilution with serum-free medium and centrifugation (440×g for 10 minutes). Following one rinse with phosphate-buffered saline (0.137 M NaCl; 2.7 mM KCl; 8.1 mM $Na_2HPO_4$; 1.4 mM $KH_2PO_4$; pH 7.2) (PBS), cells were either resuspended in PBS (pH 7.2) to assay for CE formation or lysed in SLS buffer (50 mM Tris; 10 mM EDTA, pH 8.0; 0.5% (w/v) sodium lauroyl sarcosine) to determine DNA fragmentation. Control controls consisted of adherent keratinocytes treated for similar times in 3 parts Ham's F-12 plus 1 part DME.

Northern Analysis

Cells were grown in standard keratinocyte culture medium on a 3T3 feeder layer. The feeder layer was removed 24 hours prior to RNA isolation with 0.02% EDTA in PBS. Poly A⁺RNA was isolated from logarithmically growing cells as previously described (Sadek and Allen-Hoffmann, 1994). Poly A⁺RNA was electrophoresed in a 1.2% agarose gel containing formaldehyde and electroblotted to a Zeta-probe membrane (Bio-Rad Laboratories, Richmond, Calif.). The membrane was prehybridized and then hybridized in the presence of a random primer [$^{32}$p]-dCTP-labeled cDNA probe as recommended by the supplier. The cDNA probes used for detection include rat glyceraldehyde-3-phosphate dehydrogenase, pGPDN5 (Fort, et al., 1985), monkey TGF-β1 (Sharples, et al., 1987), EGF receptor (Xu, et a., 1984), mouse keratin 14 (gift from Dennis Roop), TGF-α (Kudlow, et al., 1988), and a 830-bp 5' fragment of human c-myc (Miyamoto, et al., 1989).

Cornified Envelope (CE) Formation

Keratinocytes were removed from culture plates and recovered from suspension as described previously. Cells from each treatment were counted and resuspended in triplicate at $10^6$ cells/ml in PBS (pH 7.2) containing 1% SDS and 20 mM dithiothreitol. Samples were boiled for 5 minutes in a waterbath and cooled to room temperature. DNase (0.5 μg/ml) was added and CEs counted using a hemacytometer. CE formation was calculated as a percentage of input cells.

Analysis of Nucleosomal DNA Fragmentation

DNA was isolated and labeled as previously described (Sachsenmeier and Allen-Hoffmann, 1996). Briefly, $2.5 \times 10^6$ cells were lysed in 500 μl of 50 mM Tris, 10 mM EDTA pH 8.0 and 0.5% (w/v) sodium lauroyl sarcosine. The lysate was extracted with phenol:chloroform:isoamyl alcohol (25:24:1, v:v:v) and ethanol precipitated. The DNA was dissolved in 20 μl TE buffer, pH 8.0, and quantitated by absorption at 260 nm. Intact and fragmented DNA was 3' end-labeled with [$α^{32}$P]-ddATP using terminal dideoxynucleotidylexotransferase as described by Tilly and Hsueh (1993). One half of each labeled sample was loaded onto a 1.5% agarose gel and electrophoresed. Gels were dried with heat using an SE 1200 Easy Breeze (Hoefer Scientific, San Francisco, Calif.) and exposed to Kodak Biomax MR film.

Formation of Organotypic Cultures

Organotypic cultures were grown as previously described (N. Parenteau, 1994). A collagen raft was formed by mixing normal human neonatal fibroblasts, CI-1-F, with Type I collagen in 10% FCS+F12+penicillin/streptomycin. Rafts were allowed to contract for 5 days. The parent cells, BC-1-Ep (5°) and the BC-1-Ep/SL (38°) cells were plated on the rafts at $3.5 \times 10^5$ cells in 50 μl 0.2% FCS+3F12:1DME+HC+Ade+Ins+CT+P/S containing 1.88 mM calcium. Cells were allowed to attach 2 hours before adding an additional 13 mls of media (Day 0). On Day 1 and 2 cells were refed. On Day 4, cells were lifted to the air interface with cotton pads and switched to cornification medium (2% FCS+3F12:1DME+HC+Ade+Ins+CT+P/S containing 1.88 mM calcium). Cells were fed cornification medium every three days. On Day 15 rafts were fixed with freshly made modified Karnovsky's fixative consisting of 3% glutaraldehyde and 1% paraformaldehyde in 0.1 M cacodylate buffer, pH 7.4, at room temperature for 3 hours. Before removing the culture media, fixative was gently added to the cells on top of the raft to prevent cornified layers from floating away. Subsequently, the culture media was aspirated and the culture wells filled with fixative. The raft was cut in half with one half processed for light microscopy and the other half for electron microscopy.

Tissue Sectioning

Fixed rafts were embedded in paraffin, sectioned and stained with hematoxylin and eosin by Surgical Pathology, University Hospital, Madison, Wis. Stained sections were viewed and photographed using an Olympus IX-70 microscope equipped with a 35 mm camera.

Electron Microscopy

Fixed cultures were washed 3 times with 0.1M cacodylate buffer, pH 7.4. Under a dissecting microscope, a scalpel was used to detach the polyester mesh supporting the raft culture from the plastic insert. The raft was cut with a scalpel into approximately 2 mm×4 mm pieces which were stored overnight in buffer. Following postfixation with 1% osmium tetroxide at 4° C., the keratinocytes were washed 4 times, 15 minutes each, with 0.1 M maleic acid, pH 6.5, before en bloc staining with 2% aqueous uranyl acetate for 1 hour. After washing with distilled water, keratinocytes were dehydrated with increasing concentrations of ethanol, 100% propylene oxide, and infiltrated with 1:1 propylene oxide:eponate overnight. Rafts were embedded in fresh Eponate in flat embedding molds and oriented so they could be sectioned perpendicularly on a Reichert Ultracut E3 ultramicrotome equipped with diamond knife. Thin sections were stained with lead citrate and examined in a Hitachi H-7000 electron microscope (Hitachi, San Jose, Calif.) operated a: 75 kV.

Transfection Cell Culture

For transfection experiments, BC-1-Ep/SL cells were plated at a density of $3 \times 10^5$ cells onto mitomycin C-treated Swiss mouse 3T3 fibroblasts in 100 mm dishes. Cells were given 48 hours to adhere at which time the 3T3 layer was removed with 0.5 mM EDTA. Cells were rinsed twice with DME and serum-containing media was added. Cells were transfected 24 hours later.

Plasmid DNA

Plasmid DNA was prepared with the Endotoxin Free Maxiprep Kit (Qiagen). pGreenLantern was linearized using XmnI. pcDNA3 neo and pTracer-SV40 (Invitrogen) were linerarized using BglII (Promega). Expression of green fluorescent protein (GFP) is driven by a constitutively active CMV promoter in both pGreenLantern and pTracer-SV40 plasmids.

Determination of Optimal Conditions for Transfection of BC-1-Ep/SL Cells

BC-1-Ep/SL cells passage 30°-40° were transfected using the polycationic lipid GeneFECTOR (VennNova). The transfection mix is made by adding 20–33 μg linearized plasmid DNA to 500 μl sterile milli-Q water for each 100 mm dish. Different amounts of GeneFECTOR were added depending on the ratio of total DNA to GeneFECTOR which varied from 1:2 to 1:4. The transfection mix was swirled gently and incubated for 15 minutes at room temperature. Media was removed from the BC-1-Ep/SL cells, plates were rinsed twice with DME and refed with 5 mls of DME. The transfection mix was added to each plate in a drop-wise fashion and cells were incubated for 5 hours at 37° C. under 5% $CO_2$. The medium was removed and cells were rinsed twice with DME and refed with serum-containing media. The cells were viewed 24 hours post-transfection with an IX-70 inverted fluorescent microscope (Olympus) equipped with a GFP short band pass filter to check for successful transfection before analysis or flow activated cell sorting (FACS).

Optimal Transient Transfection Efficiency

BC-1-Ep/SL cells passage 30°–40° were transfected using the polycationic lipid GeneFECTOR (VennNova). The transfection mix was made by adding 15 μg linearized pGreenLantern and 5 μg pcDNA3neo (20 μg total DNA) to 500 μl sterile milliQ water for each 100 mm plate of cells. Genefector is then added at a quantity of three times that of the total DNA (1:3 ratio of DNA to GeneFECTOR). The transfection mix was swirled gently and incubated for 15 minutes at room temperature. Media was removed from the BC-1-Ep/SL cells, plates were rinsed twice with DME and refed with 5 mls of DME. The transfection mix was added to each plate in a dropwise fashion and cells were incubated for 5 hours at 37° C. under 5% $CO_2$. The medium was removed and cells were rinsed twice with DME and refed with keratinocyte media. The cells were viewed as described previously.

Flow Cytometry

Twenty-four hours post-transfection, BC-1-Ep/SL cells were removed from culture with 0.5 mM EDTA and 0.1% trypsin. After short centrifugation (440×g for 5 minutes), cells were resuspended in serum-containing medium at $2\times10^6$ cells/ml. 500 μl of this cell suspension was filtered through 42 μm mesh (Tetko, Inc.) and stained with 5 μg/ml propidium iodide (PI) immediately prior to analysis. Transfected BC-1-Ep/SL cells were analyzed on either a FACScan or FACSCalibur benchtop flow cytometer (both from Becton Dickinson) equipped with a laser tuned to 488 nm. Ten thousand events were acquired and analyzed using CellQuest software (Becton Dickinson) and analysis was restricted to live events only, based on PI staining. Cell viability and transient transfection efficiency data were obtained.

Cell Sorting

We used the following protocol to obtain stable GFP-expressing BC-1-Ep/SL cells. Twenty-four hours post-transfection, cells were removed using 0.5 mM EDTA and 0.1% trypsin. After short centrifugation (440×g for 5 minutes), cells were resuspended in serum-containing medium at a density of $5-7\times10^6$ cells/ml. This suspension was then filtered through 42 μm sterile mesh (Tetko, Inc.). Immediately prior to sorting cells were stained with 5 μg/ml propidium iodide. Transfected BC-1-Ep/SL cells were sorted on a FACStar Plus (Becton Dickinson) equipped with a coherent argon laser tuned to 488 nm. Transfection efficiency data was obtained with CellQuest software (Becton Dickinson). Cells were sorted at a rate of 2000/second and samples were collected post-sort to check viability and GFP expression.

Colony Forming Efficiency

Colony forming efficiencies (CFE) were obtained by plating 1000 events onto duplicate 60 mm plates in the presence of mitomycin C-treated Swiss mouse 3T3 fibroblasts. After one week, plates were fixed for 10 minutes in 10% formalin, rinsed with tap water, and stained overnight with methylene blue. Colonies were counted and divided by the number of events plated to obtain the final CFE. Based on the CFE calculated, the total number of colonies formed was obtained by multiplying the number of events by the CFE. GFP-expressing colonies were counted 10–12 days post-sorting using an IX-70 inverted fluorescent microscope with a GFP short band pass filter. The number of GFP-expressing colonies was divided by the total number of colonies formed to obtain a stable GFP expressing colony forming efficiency.

Isolation and Identification of Stable pGreenLantern Transfected BC-1-Ep/SL cells BC-1-Ep/SL cells were transfected with pGreenLantern as described previously and sorted based on fluorescence. Immediately following cell sorting, GFP-positive PC-1-Ep/SL cells were reinitiated into culture. Cells were plated at low density from $2-3\times10^4$ cells per 100 mm dish onto mitomycin C-treated Swis mouse 3T3 fibroblasts. Cells were monitored every other day using an IX-70 inverted fluorescent microscope (Olympus) with a GFP short band pass filter. Non-GFP expressing colonies were removed by scraping and stable GFP expressing colonies were allowed to expand. When GFP expressing colonies had grown to an estimated density of 1000 cells or more, they were isolated by ring cloning and replating onto 60 mm plates with ring mitomycin C treated 3T3's and expanded.

Isolation and Identification of Stable pTracer-SV40 Transfected BC-1-Ep/SL cells BC-1-Ep/SL cells were transfected using 20 μg of pTracer-SV40 and a 1:4 ratio of DNA to GeneFECTOR (VennNova). Twenty-four hours post-transfection cells were removed with 0.5 mM EDTA, 0.1% trypsin and resuspended at a density of $2\times10^6$ cells/ml in serum containing medium. Three $\times10^6$ cells were replated onto two 100 mm plates with a mitomycin C-treated Swiss mouse 3T3 fibroblasts. Forty-eight hours after passage, GFP-positive cells were selected for 5 days with 250 μg/ml zeocin (Invitrogen). Stable GFP-expressing BC-1-Ep/SL cells were purifiedusing sterile cell sorting and expanded as described previously.

Histological Analysis of Transfected Organotypic Cultures

GFP-expressing BC-1-Ep/SL cells at 43(passage were plated at a density of $3\times10^5$ cells/collagen raft and grown in organotypic culture for 16 days. Raft cultures were fixed for at least one hour in 4% paraformaldehyde before embedding in paraffin. Five μm sections were cut and alternate sections were stained with hemotoxylin and eosin (H&E) by Surgical Pathology, UW-Madison. Non-H&E sections were rehydrated, stained with 5 μg/ml Hoechst dye (33258) for 15 minutes, dehydrated and mounted using Cytoseal mounting media (Stephens Scientific). Sections were viewed and photographed using an IX-70 inverted fluorescent microscope (Olympus) equipped with a dual FITC-Hoechst filter.

Analysis of GFP Expression by Confocal Microscopy

GFP-expressing BC-1-Ep/SL cells at 43° passage were plated at a density of $3\times10^5$ cells/collagen raft and grown in organotypic culture for 16 days. Raft cultures were fixed overnight in 4% paraformaldehyde-PBS and rinsed for one hour in a 0.1 M glycine-PBS solution at 4°. Whole rafts were mounted, coverslipped using Vectashield mounting media (Vector labs) and sealed with rubber cement. GFP expression was analyzed using a confocal laser scanning microscope (Nikon Diaphot 200) with excitation at 488 nm and detection at 500–530 nm bandpass filter. Images were taken at 10 μm intervals starting at the upper cornified layer. The microscope is located in the W. M. Keck Neural Imaging Laboratory, University of Wisconsin-Madison.

B. Results

Isolation of the BC-1-Ep/SL Cell Line

Cells were desegregated from a neonatal foreskin by trypsinization. Keratinocytes were initiated into culture by plating an aliquot of the cell suspension onto a mitomycin C-treated Swiss mouse 3T3 feeder layer in standard keratinocyte growth medium containing 0.66 mM calcium. Fibroblasts were initiated into culture by plating an aliquot of cell suspension onto a tissue culture plate containing Ham's F-12 medium supplemented with 10% fetal calf serum.

After approximately 9 days, primary cultures of keratinocytes designated strain BC-1-Ep were cryopreserved and subcultured onto a feeder layer. Fibroblast cultures were grown to near confluency and also cryopreserved. In early passages, the BC-1-Ep cells exhibited no morphological or growth characteristics that were atypical for cultured normal human keratinocytes. Cultivated BC-1-Ep cells exhibited stratification as well as features of programmed cell death.

To determine replicative lifespan, the BC-1-Ep cells were serially cultivated to senescence in standard keratinocyte growth medium at a density of $3\times10^5$ cells per 100 mm dish. By passage 15 most keratinocytes in the population appeared senescent as judged by the presence of numerous abortive colonies which exhibited large, flat cells.

However, at passage 16, keratinocytes exhibiting a small cell size were evident. By passage 17, only the small sized keratinocytes were present in the culture and no large, senescent keratinocytes were evident. The resulting population of small keratinocytes that survived crisis appeared morphologically uniform and produced colonies of keratinocytes exhibiting typical keratinocyte characteristics including cell-cell adhesion and apparent squame production.

The keratinocytes that survived senescence were serially cultivated at a density of $3 \times 10^5$ per 100 mm dish for 59 passages, demonstrating that the cells had achieved immortality. The keratinocytes which emerged from the original senescencing population are termed BC-1-Ep/spontaneous line (BC-1-Ep/SL).

Cytogenetic Analysis and DNA Fingerprinting

Chromosomal analysis was conducted on the parental BC-1-Ep cells at passage 3 and BC-1-Ep/SL cells at passages 31 and 54. The parental BC-1-Ep cells have a normal chromosomal complement of 46, XY. At passage 31 all BC-1-Ep/SL cells contained 47 chromosomes due to an extra isochromosome of the long arm of chromosome 8 (FIG. 1). No other gross chromosomal abnormalities or marker chromosomes were detected. At passage 54 all cells contained the isochromosome 8, however, an additional isochromosome of the long arm of chromosome 1 and a marker chromosome were present in a small fraction of the population (Table 1 in Appendix 1). The BC-1-Ep/SL cells have been screened for the presence of proviral HIV DNA sequences and found to be negative. Regions of the HIV provirus were amplified enzymatically, hybridized to radio-labelled HIV-1 specific DNA probes, and the amplified DNA separated by size and visualized using agarose gel electrophoresis and autoradiography. Polymerase chain reaction products were compared by size and specificity to known HIV-1 positive and negative controls. The presence of HPV16, and 31 viral sequences were assessed by Southern analysis and none were detected.

The DNA fingerprints for the BC-1-Ep/SL cell line and the BC-1-Ep keratinocytes are identical at all twelve loci. The odds of the BC-1-Ep/SL cell line having the parental BC-1-Ep DNA fingerprint by random chance is $4 \times 10^{-16}$. The DNA fingerprints for ED-1-Ep, SCC4 and SCC13y are different from the BC-1-Ep pattern. The data from our DNA fingerprint analysis of the BC-1-Ep/SL cell line proves it arose from the parental BC-1-Ep cells. This data also shows that keratinocytes isolated from other humans, ED-1-Ep, SCC4, and SCC13y, are unrelated to the BC-1-Ep cells or each other. The BC-1-Ep/SL DNA fingerprint data provides an unequivocal way to identify the BC-1-Ep/SL cell line.

BC-1-Ep/SL Keratinocytes are Not Tumorigenic in Athymic Nude Mice

To determine the tumorigenicity of the parental BC-1-Ep keratinocytes and the immortal BC-1-Ep/SL keratinocyte cell line, cells were injected into the flanks of athymic nude mice. The human squamous cell carcinoma cell line, SCC 4, was used as a positive control for tumor production in nude mice. The injection of samples was designed such that each animal received an injection of SCC 4 cells in one flank and either the parental BC-1-Ep keratinocytes or the BC-1-Ep/SL cells in the opposite flank. This injection strategy eliminated animal to animal variation in tumor production and confirmed that the mice would support vigorous growth of tumorigenic cells. Neither the parental BC-1-Ep keratinocytes (passage 6) nor the BC-1-Ep/SL keratinocytes (passage 35) produced tumors in nude mice. The results of the tumorigenicity testing is shown in Table 2 in Appendix 1.

Growth Characteristics in vitro

BC-1-Ep/SL keratinocytes are nontumorigenic and exhibit morphological characteristics of normal human keratinocytes when cultured in standard keratinocyte growth medium in the presence of mitomycin C-treated 3T3 feeder cells. To further evaluate the growth characteristics of the BC-1-Ep/SL cells, we examined the steady state mRNA levels of known autocrine regulators of keratinocyte growth. Northern analysis of mRNAs from the BC-1-Ep/SL cell line revealed that expression of autocrine growth factors, such as transforming growth factor-$\alpha$ (TGF-$\alpha$) and transforming growth factor-$\beta$ (TGF-$\beta$), as well as the levels of epidermal growth factor receptor (EGFR) and c-myc, are similar, if not identical to the parental BC-1-Ep keratinocytes.

We next determined which constituents of standard keratinocyte growth medium are required for optimal growth of BC-1-Ep/SL cells. Serial cultivation in the absence of epidermal growth factor (EGF) resulted in a 60 to 90% reduction in cell number at each passage, compared to EGF-containing control cultures (FIG. 1). The dependence on EGF for growth of BC-1-Ep/SL cells appears to be a stable characteristic. BC-1-Ep/SL cells at passage 50 continue to exhibit a dependence on EGF for optimal growth.

Figure 3:
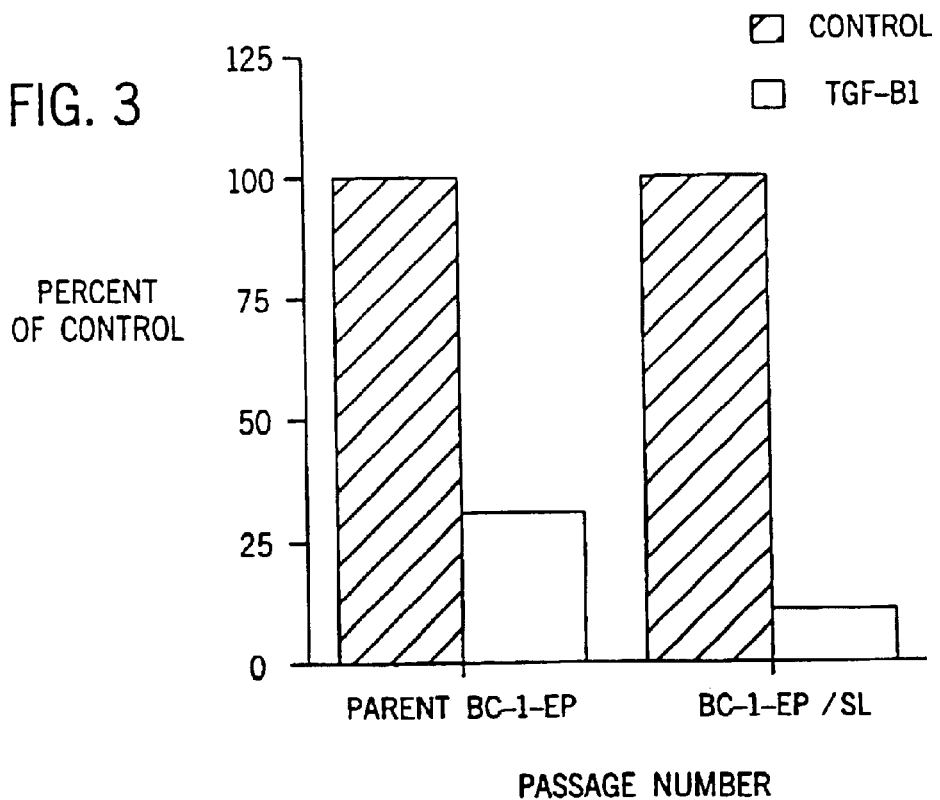
FIG. 3 demonstrates that transforming growth factor-β-1 (TGF-β1) inhibits growth of BC-1-Ep/SL keratinocytes. The parent cells, BC-1-Ep (6°) and BC-1-Ep/SL (28°) were plated in standard media without EGF or a 3T3 feeder layer. Cells were treated +/−5 ng/ml TGF-β1 when the cells were ~20% confluent in standard media without EGF. Cells were counted 3–5 days later. The effect of TGF-β1 treatment is shown as a percentage of controls.

Another polypeptide growth factor that plays an important role in epidermal homeostasis is transforming growth factor-$\beta 1$ (TGF-$\beta 1$). In vitro, TGF-$\beta 1$ is an inhibitor of growth in cultured normal human keratinocytes (Pientenpol, et al., 1990), however malignant transformation of keratinocytes often results in attenuation of TGF-$\beta 1$-induced growth inhibition (Bascom, et al., 1989; Parkinson, et al., 1983; Pietenpol, et al., 1990; Rice, et al., 1992). Like the normal parental BC-1-Ep keratinocytes, TGF-$\beta 1$ inhibits the growth of the BC-1-Ep/SL cell line (FIG. 3). The TGF-$\beta 1$-induced growth inhibition is reversible in both the parental and BC-1-Ep/SL keratinocytes.

Figure 4:
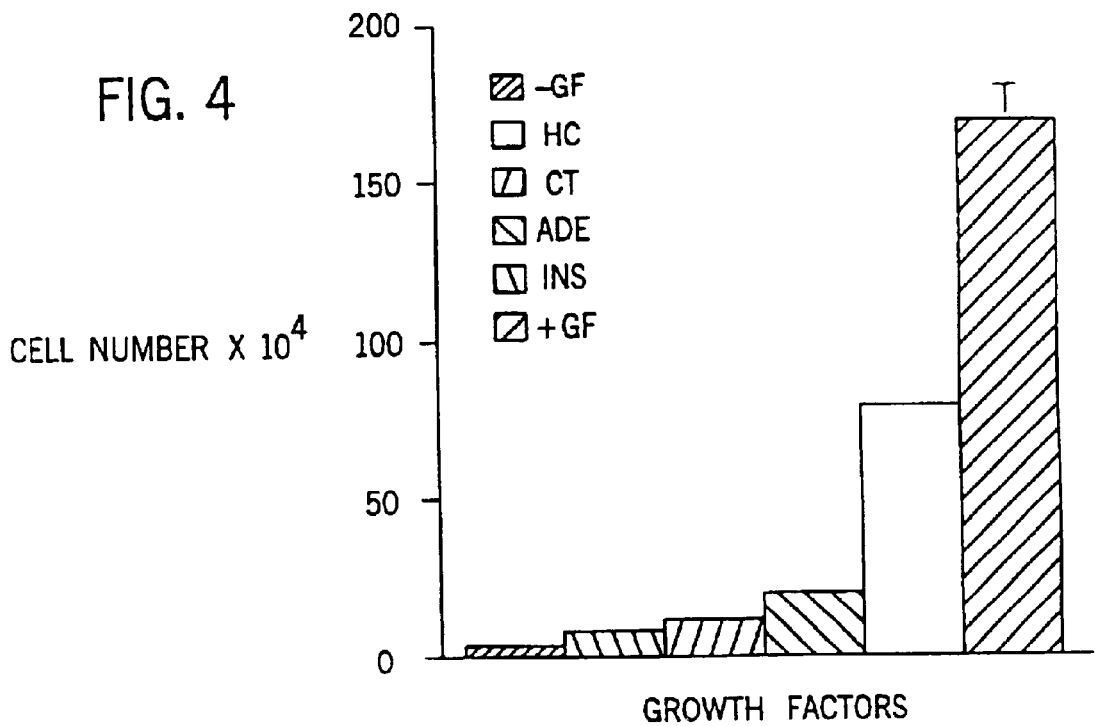
FIG. 4 demonstrates growth factor requirements of BC-1-Ep/SL cells. BC-1-Ep/SL cells at passage 31 were grown in 2.5% FCS+3F12:1DME+10 ng/ml EGF supplemented with no additional growth factors (−GF), 0.4 μg/ml hydrocortisone (HC), 8.4 ng/ml cholera toxin (CT), 24 μg/ml adenine (Ade), 5 μg/ml insulin (Ins), or all growth factors (+GF). Cell growth increased in the presence of each growth factor alone, however optimal growth was achieved in the presence of all growth factors.

To further characterize the requirements for optimal in vitro growth of the BC-1-Ep/SL keratinocytes, cultures were cultivated in medium supplemented with 2.5% fetal calf serum, EGF, and individual constituents of the standard growth medium. FIG. 4 demonstrates that addition of insulin alone promotes a 15-fold increase in cell number. However, addition of all constituents of standard keratinocyte growth medium promotes a 30-fold increase in BC-1-Ep/SL cell number. These findings demonstrate that the BC-1-Ep/SL cell line has maintained cell type-specific requirements for growth in vitro.

Differentiation Characteristics in vitro

We next investigated whether BC-1-Ep/SL cells could undergo normal differentiation in both surface culture and organotypic culture. We monitored a marker of squamous differentiation, the formation of cornified envelopes (CE). In cultured human keratinocytes, early stages of CE assembly result in the formation of an immature cornified envelope composed of involucrin, cystatin-a and other proteins, which represent the innermost third of the mature cornified envelope. We examined CE formation in the parental cells and the BC-1-Ep/SL keratinocytes (Table 3 in Appendix 1). Less than two percent of the keratinocytes from either the adherent parental cells or the BC-1-Ep/SL cell line produce CE's. This finding is consistent with our previous studies demonstrating that actively growing, subconfluent keratinocytes produce less than five percent CE (Hines and Allen-Hoffmann, 1996). To determine whether the BC-1-Ep/SL cell line is capable of producing CE's when induced to differentiate, the cells are removes from surface culture and placed in suspension for 24 hours in medium made semi-solid with methylcellulose. Many aspects of terminal differentiation, including differential expression of keratins (Drozdoff and Pledger, 1993) and CE formation (Green, 1977) can be triggered in vitro by loss of keratinocyte cell-cell and cell-substratum adhesion. We found that the BC-1-Ep/SL keratinocytes produced as many and usually more CE's, than the parental keratinocytes (Table 3 in Appendix 1). These findings demonstrate that the BC-1-Ep/SL keratinocytes are not defective in their ability to make this cell type-specific differentiation structure.

BC-1-Ep/SL Cells Undergo Apoptosis Following Loss of Adhesion

We next determined whether BC-1-Ep/SL keratinocytes undergo apoptosis by assaying nucleosomal cleavage of DNA. Specific DNA cleavage into oligonucleosomal fragments is a hallmark of apoptosis (Arends, et al., 1990; Wyllie, 1980). Keratinocytes from all species studied to date can undergo apoptosis both in vivo and in vitro. Epidermal keratinocytes are destined to enucleate and lose metabolic activity as part of their differentiation pathway. Many parallels exist between keratinocyte terminal differentiation and apoptosis. We assessed the ability of the parental and BC-1-Ep/SL keratinocytes to undergo nucleosomal cleavage following suspension. Normal cultured human keratinocytes exhibit both morphological and biochemical features of apoptosis when deprived of cell-cell and cell-substrata contact by suspension in semi-solid medium. Adherent, preconfluent keratinocytes from parental or BC-1-Ep/SL cell line grown in serum-free, additive-free medium for 24 hours exhibited no detectable DNA fragmentation. Similarly, adherent cells treated for an identical time with semi-solid, serum-free, additive-free medium did not exhibit nucleosomal fragmentation. When suspended in semi-solid medium both the parental and BC-1-Ep/SL keratinocytes exhibited DNA fragmentation. These findings are consistent with previous studies from our laboratory demonstrating that normal human keratinocytes induced to differentiate by loss of adhesion will fragment their DNA (Hines and Allen-Hoffmann, 1996a, b; Sachsenmeier, et al., 1996). Taken together, these data demonstrate that the BC-1-Ep/SL keratinocytes are capable of differentiating and respond normally to cell type-specific signals to undergo apoptosis.

Organotypic Cultures of BC-1-Ep/SL Cells Exhibit Normal Squamous Differentiation To confirm that the BC-1-Ep/SL keratinocytes can undergo normal squamous differentiation, the cells were cultivated in organotypic culture. Differentiation of keratinocytes cultured on a plastic substrata under medium promotes growth and limited differentiation. Specifically, human keratinocytes become confluent, stratify and produce a multilayered sheet that is similar to stratified epithelium. However, by light and electron microscopy there are striking differences between the architecture of the multilayered sheets formed in tissue culture and intact human skin. Organotypic culture is a technique to culture keratinocytes under in vivo-like conditions. Specifically, the cells adhere to a physiological substrata, fibrillar collagen embedded with dermal fibroblasts, and are lifted to the air-medium interface so that the cells can grow with their upper sheets air-exposed and with the proliferating basal cells closest to the gradient of nutrients provided by diffusion through the collagen gel. Under these conditions, correct tissue architecture is formed.

We compared both the parental cells, BC-1-Ep 5°, and the cell line, BC-1-Ep/SL 38°, grown in organotypic culture. Several characteristics of a normal differentiating epidermis are evident. In both the parental cells and the BC-1-Ep/SL cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the BC-1-Ep parental cells and the BC-1-Ep/SL cells. The appearance of flattened squamous cells is evident in upper layers of keratinocytes located above the basal layer and demonstrates that stratification has occurred. In the uppermost part of the tissue (A and B), the enucleated squames are shown peeling off the top of the culture. To date, we have not observed any histological differences in differentiation at the light microscope level between the parental BC-1-Ep keratinocytes, and BC-1-Ep/SL keratinocyte cell line grown in organotypic culture.

To confirm our histological observations, BC-1-Ep 6° and BC-1-Ep/SL 38° were analyzed using electron microscopy. Higher magnification allowed us to observe more detailed characteristic structures of normal differentiation in the raft cultures. Examination of micrographs convinced us that BC-1-Ep/SL cells undergo normal stratification in organotypic culture. This was similar to what was seen with the parental BC-1-Ep cells (data not shown). We also noted the formation of hemidesmosomes in the basal layer, which also suggests that the cell line is able to form structures found in normal human epidermis. Hemidesmosomes are specialized structures which increase adhesion of the keratinocytes to the basal lamina and help maintain the integrity and strength of the tissue. Both the light level and electron microscopy data demonstrate that the BC-1-Ep/SL cell line can stratify and differentiate normally in organotypic culture.

Optimal Transient Transfection Efficiency of the BC-1-Ep/SL Cell Line

We have chosen to use the plasmid, pGreenLantern, which contains the gene for green fluorescent protein (GFP) as a marker of transfection. GFP is a naturally fluorescing, non-toxic protein form jellyfish which is easily seen when exposed to UV light. In addition, some experiments included co-transfection of pGreenLantern with another plasmid, pcDNA3neo, which contains a gene for neomycin resistance allowing cells to grow in the presence of G418. However, use of G418 as a selection method can be extremely toxic to keratinocytes and may inadvertently kill positively transfected cells. We believe that sterily sorting cells based on GFP expression will provide a quick way to select for positive transfectants and is the least toxic selection method available at present.

There have been many parameters to consider in optimization of transfection in this system. We have narrowed these down to the three most essential for obtaining the maximum transfection efficiency. These parameters include cell confluence, total amount of DNA (concentration) and the ratio of DNA to transfection reagent (GeneFECTOR). Transfections are completed using set parameters and cells are analyzed the following day with an inverted fluorescent microscope for presence of GFP expression. In addition, flow cytometry is use to obtain information on the viability and number of GFP positive cells.

Figure 5:
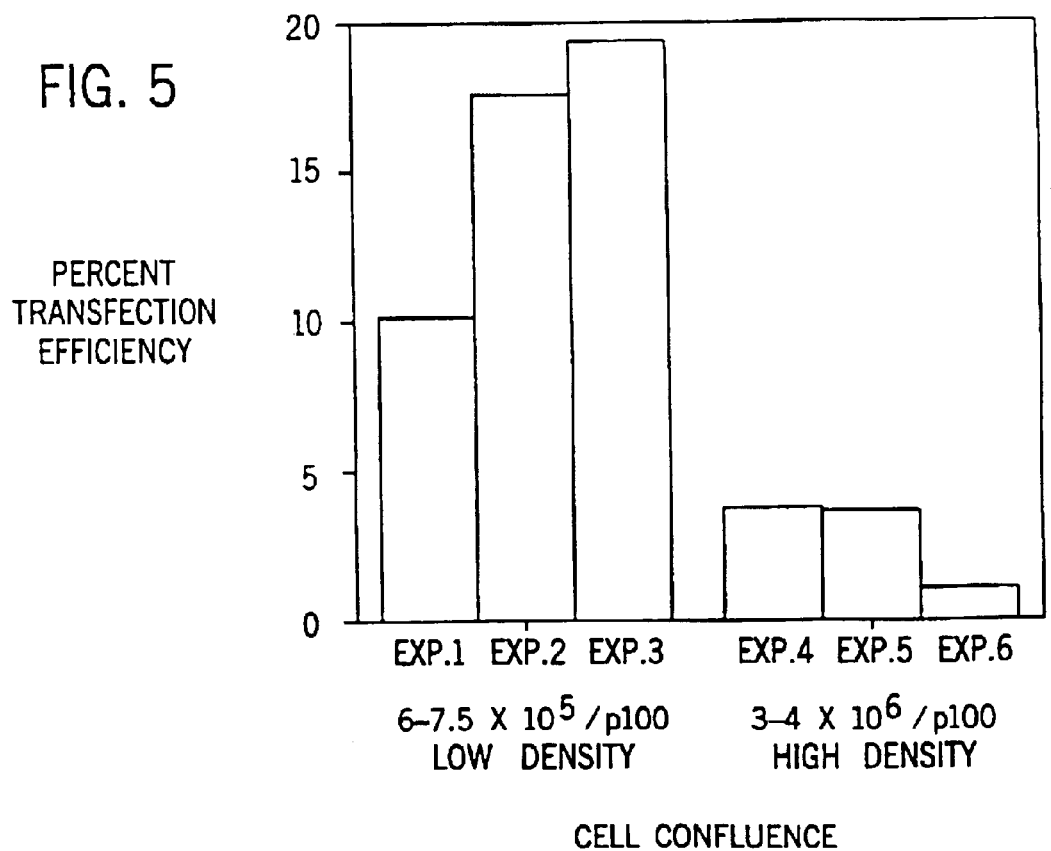
FIG. 5 shows that increased cell confluence reduces transient transfection efficiency in BC-1-Ep/SL cells. BC-1-Ep/SL cell were transfected with the GFP containing plasmid pGreenLantern (Gibco) and pcDNA3 neo (Invitrogen) using GeneFECTOR (VennNova Inc.). A range of 15–20 μg of linearized pGreenLantern and 5–6.7 μg of pcDNA3neo was used. Cell numbers were obtained by trypsinization and counting of keratinocytes using a hemacytometer. Low density was defined as $6–7.5 \times 10^5$ cells/100 mm dish. High density was defined as $3–4 \times 10^6$ cells/100 mm dish. Transfection efficiency was obtained using fluorescence activated cell sorting (FACS). Each bar of the graph represents a single experiment.

Cell confluence appears to be critical in obtaining the maximum transfection efficiency. BC-1-Ep/SL cells at varying levels of confluence were transfected with a range of 20–25 $\mu$g of DNA and analyzed 24 hours later by flow cytometry. Transient transfection efficiencies from several experiments suggest that a low confluence of $5-7\times10^5$ cells/100 mm dish (~30% confluent) will yield the highest transfection efficiency ranging from 10–19.5%. Transfections completed at high confluence, $2-4\times10^6$ cells/100 mm dish (~70% confluent), yielded much lower transient transfection efficiencies of 1–3% (FIG. 5).

Optimal DNA concentration was also tested using total amounts of pGreenLantern and pcDNA3neo ranging from 20–33 µg. All other parameters were held constant. We found that higher levels of total DNA do not yield better transfection efficiency. Our data suggest that a total 20 µg of DNA is optimal for the transfection of BC-1-Ep/SL cells, resulting in a transient transfection range of 3.79–13.64% (Table 4 in Appendix 1) (Cell confluence is included in this table to account for variability in transfection efficiency between experiments). We observed that higher amounts of DNA caused increased toxicity to the cells (flow cytometry, data not shown).

The third parameter examined in optimizing transfection efficiency of BC-1-Ep/SL cells was the ratio of DNA to transfection reagent. Several different ratios of DNA to GeneFECTOR were investigated, these include 1:2, 1:3, and 1:4. Transient transfection efficiencies collected from triplicate experiments indicate that a ratio of one part DNA to three parts GeneFECTOR (1:3) is optimal, with transfection efficiencies ranging from 10–19.5% (Table 5 in Appendix 1) (Cell confluence is included to account for variability in transfection efficiency between experiments). We have concluded that a cell confluence of 30% ($5-7\times10^5$ cells/100 mm dish), total of 20 µg DNA, and a 1:3 ratio of DNA to GeneFECTOR are the conditions for optimal transient transfection efficiency in the BC-1-Ep/SL cell line.

Identification and Isolation of Stable GFP Transfected BC-1-Ep/SL Cells

Using the optimized conditions for transient transfection efficiency, we have successfully isolated and obtained stable GFP-expressing BC-1-Ep/SL cells. Stable expression is defined by integration of the GFP gene into the host cell's chromosomes. From earlier observations of transiently transfected GFP positive cells, there was concern that the brightest cells, those with the highest GFP expression, may be too differentiated to maintain colony forming ability when replated in surface culture. To test this, cells were transfected and sterily sorted based on the fluorescent intensity of GFP expression from dimmest to brightest. GFP positive cells acquired from cell sorting were plated and stable colonies detected and counted 10–12 days post-sort. Variability of GFP expression in these colonies was noted. The larger differentiated cells appear to have brighter GFP expression. The stable, GFP positive colony forming efficiency (CFE) was calculated as described previously. Three separate cell sorting experiments have been completed and the percentage of stable GFP positive cells was calculated to be 3.2%, 4.7%, and 5.64%. A sample table which represents one of these experiments is shown (Table 6 in Appendix 1). Data obtained in triplicate experiments suggest those cells with the greatest GFP fluorescence appear to have lower colony forming efficiency than less GFP fluorescent cells. The GFP positive CFE will allow us to estimate the number of GFP positive cells that need to be plated in order to obtain a reasonable number of stably transfected colonies.

As a result of the sterile sorts, we were able to isolate and expand several clonal lines of stable GFP expressing BC-1-Ep/SL cells. Lines expressing GFP from both pTracer-SV40 and pGreenLantern vectors have been serially passaged with no apparent changes in cell morphology or decrease in GFP expression.

Stable Transfectants of BC-1-Ep/SL Keratinocytes Expressing Green Fluorescent Protein Exhibit Normal Stratification in Organotypic Culture To test the ability of the stably transfected GFP positive BC-1-Ep/SL cells to recreate normal tissue architecture, we plated these cells into organotypic culture. This type of culture allows the cells to display as many characteristics of intact skin as possible in a three dimensional microenvironment. This procedure has been repeated in triplicate and the resulting tissue analyzed histologically by fluorescent microscopy as well as confocal microscopy (data not shown). It appears that the stably transfected cells differentiate similarly to an untransfected BC-1-Ep/SL control. Both cultures show comparable cell stratification with no noticeable histological differences at the light microscope level. Interestingly, the appearance of GFP is most intense in the differentiated upper layers of the culture. We have observed this expression pattern with both fluorescent and confocal microscopy. The differences in GFP intensity maybe the result of variations in the amount of protein accumulated in the cell layers. Alternatively, the CMV promoter driving GFP expression may not become active until the cell reaches a more differentiated state.

2. Use of the Spontaneously Immortalized Human Keratinocyte BC-1-Ep/SL in an Organotypic Culture System to Model Growth of Human Squamous Cell Carcinoma A. Materials and Methods Description of Cellular Components The BC-1-Ep/SL cell line is a spontaneously immortalized human keratinocyte cell line which maintains normal keratinocyte growth and differentiation characteristics. It was isolated using standard for growth of primary keratinocytes from neonatal human foreskin samples. Keratinocyte cultures were established by plating aliquots of a single cell suspension in the presence of mitomycin C-treated Swiss Mouse 3T3 fibroblasts as described by Allen-Hoffmann and Rheinwald (Rheinwald, J. G., et al., 1981).

The MW-1-F fibroblasts were isolated from a normal human neonate and cultivated following standard methods for trypsin disaggregation of neonatal foreskin. The culture was initiated by plating an aliquot of the disaggregated cell suspension onto a tissue culture plate containing Ham's F-12 medium supplemented with 10% fetal calf serum. Secondary and subsequent passage of fibroblast cultures are used as part of the non-epidermal component of the organotypic culture model as described below.

The SCC13y cell line serves as the prototype H&N malignant cell line for development of the organotypic co-culture model. SCC13y was subcultured from the SCC13 cell line. SCC13 is derived from a tumor of the facial epidermis which had recurred following radiotherapy (Rheinwald, J. G., et al., 1981). A collagenase disaggregation protocol was used to produce a single cell suspension from a surgical biopsy of the tumor. The cell suspension was plated onto a mitomycin C 3T3 fibroblast feeder layer to allow isolation and expansion of the primary culture. The SCC13 cell line was established by continual passage in culture and maintained the aneuploid karyotype of the tumor from which it was derived. SCC13y maintains a limited ability to differentiate following methylcellulose suspension, a technique which promotes expression of certain differentiation markers and structures in normal keratinocytes. However, SCC13y is tumorigenic in nude (athymic) mice.

Cell Culture

BC-1-Ep/SL cells are grown in standard keratinocyte growth media. Standard keratinocyte culture medium is a mixture of Ham's F12:Dulbecco's modified Eagle's medium (DME), (3:1, 0.66 mM calcium) supplemented with 2.5% fetal clone II (FCII-is a fetal calf serum substitute from Hyclone), 0.4 µg/ml hydrocortisone (HC), 8.4 ng/ml cholera toxin (CT), 5 µg/ml insulin (Ins), 24 µg/ml adenine (Ade), 10 ng/ml epidermal growth factor (EGF), 100 units penicillin and 100 µg/ml streptomycin (1% P/S). The cells are passaged at weekly intervals at $3\times10^5$ cells on a 100 mm² tissue culture dish with a mitomycin C inactivated Swiss mouse 3T3 fibroblast feeder layer.

MW-1-F fibroblasts stocks are maintained in DME supplemented with 10% calf serum and passaged weekly on 100 mm² tissue culture dishes.

SCC13y cell line stocks are maintained in SCC medium (DME supplemented with 5% FCII, 0.4 µg/ml HC, and 1% P/S). The cells are passaged weekly on a 100 mm² tissue culture dish with a mitomycin C inactivated Swiss mouse 3T3 fibroblast feeder layer.

Formation of Organotypic Cultures

Figure 2:
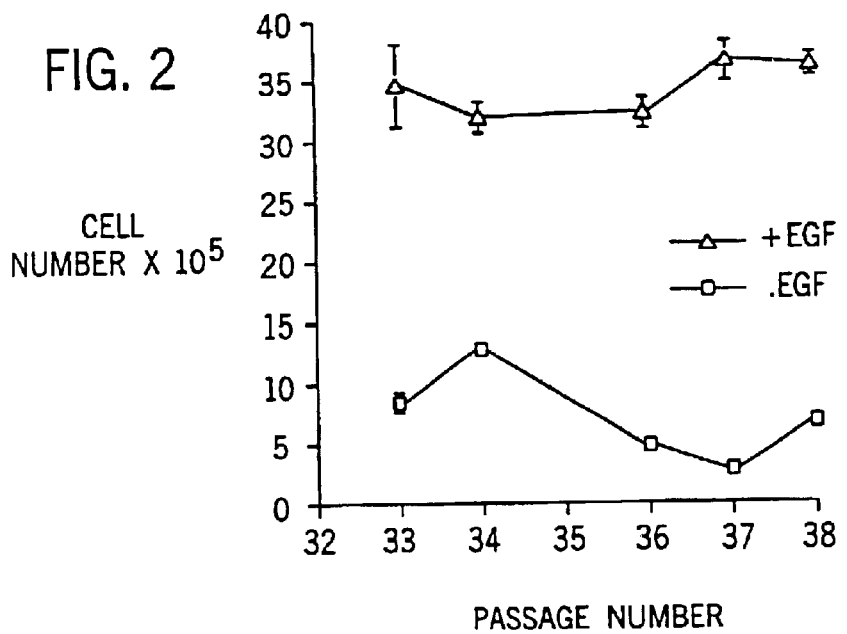
FIG. 2 demonstrates the requirement for epidermal growth factor (EGF) for serial passage of EC-1-Ep/SL cells. BC-1-Ep/SL cells were serially passaged in standard media +/−10 ng/ml EGF. The cells survived without EGF but grew poorly.

Organotypic cultures were grown as previously described (Parenteau, N., 1994). This procedure was modified to allow growth of tumor foci within a reconstructed epidermal/dermal skin equivalent (FIG. 2). A collagen base was formed by mixing normal human neonatal fibroblasts, MW-1-F (50), with Type I collagen in 10% FCII+F-12+penicillin/streptomycin. The collagen bases were allowed to contract for 5 days. BC-1-Ep/SL (31°) cells were plated onto the collagen base at $3.5\times10^5$ cells in 50 µl 0.2% FCS+3F12:1DME containing 1.88 mM calcium+HC+Ade+Ins+CT+P/S. For co-cultures of stratifying keratinoyctes and malignant cells, SCC13y$^{GFP+}$ cells were mixed with the BC-1-Ep/SL cells at ratios of 500, 5000, and 100,000 SCC13y$^{GFP+}$ FP cells to $3\times10^5$ BC-1-Ep/SL cells before plating (FIG. 1). Cells were allowed to attach 2 hours before adding an additional 13 mls of media (Day 0). On days 1 and 2 cells were refed. On Day 4, cells were lifted to the air interface with cotton pads and switched to cornification medium (2% FCS+3F12:1DME+HC+Ade+Ins+CT+P/S containing 1.88 mM calcium). Cells were fed cornification medium every three days. On day 15 media was removed and organotypic cultures were fixed overnight with 4% paraformaldehyde and stored in PBS with 0.1M glycine.

GFP Expression Vector and Transfection of SCC13y

A commercially available humanized green fluorescent protein (GFP) expression vector, pGreenLantern (Life Technologies, Gaithersburg, Md.) was used to genetically mark the SCC13y cell line. Expression of GFP is controlled by a constitutively active human cytomegalovirus promoter allowing GFP to accumulate in stably-transfected SCC13y cells. Plasmid DNA was prepared from vector-transformed bacterial stocks using an Endotoxin Free Maxiprep Kit (Qiagen).

For transfection experiments, SCC13y (passage 60) cells were plated at a density of $1\times10^5$ cells onto mitomycin C treated Swiss mouse 3T3 fibroblast feeder layer in 6-well plates. SCC13y cells were given 24 hours to adhere at which time the 3T3 layer was removed with 0.5 mM EDTA. SCC13y cells were rinsed twice with DME and serum-containing media was added. Cells were transfected 24 hours later.

SCC13y cells (60) were transfected using the polycationic lipid GeneFECTOR (VennNova). Herein cells transfected with GFP will be referred to as SCC13y$^{GFP+}$. Passage 10 is the first pass following transfection. The transfection mix was made by adding 10 mg of pGreenLantern to 200 ul unsupplemented DME for each well of the 6-well plate. 30 µg of GeneFECTOR was added to the DNA solution for a final 1:3 ratio of DNA to GeneFECTOR and total volume of 400 µl. The transfection mix was swirled gently and incubated for 15 minutes at room temperature in the dark. Media was removed from the SCC13y cultures, plates were rinsed twice with phosphate-free DME and refed with 2 mls of phosphate-free, unsupplemented DME. The transfection mix was added to each plate in a dropwise fashion and cells were incubated for 3 hours at 37° C. in a 5% $CO_2$ incubator, shaking every 30 minutes. The medium was removed and cells were rinsed twice with DME and refed with SCC media (no antibiotics). Twenty-four hours later media was replaced with antibiotic supplemented SCC media.

Flow Cytometry Detection and Quantification of GFP Expression

SCC13y cells were removed from culture with 0.5 mM EDTA and 0.1% trypsin 24 hours post-transfection. Cells were collected by centrifugation (440×g for 5 minutes), and resuspended in serum-containing medium at a cell density of $2\times10^6$ cells/ml and stained with 5 mg/ml propidium iodide (PI). 500 µl of this cell suspension was filtered through 42 µm mesh (Tetko, Inc.) immediately prior to analysis to remove clumps. Transfected SCC13y cells were analyzed on either a FACScan or FACSCalibur benchtop flow cytometer (both from Becton Dickinson) equipped with a 488 nm laser. Ten thousand events were acquired and analyzed using CellQuest software (Becton Dickinson). PI stained, nonviable cells were excluded from analysis. Transient transfection efficiency or percentage of SCC13y$^{GFP+}$ was calculated as the percentage of viable SCC13y$^{GFP+}$ cells out of the total number of viable cells. In experiments which determine the stability of GFP expression over time in SCC13y$^{GFP+}$ populations, the percentage of GFP-expressing cells at 4 week intervals was determined.

Isolation and Identification of Stable SCC13y$^{GFP+}$ Cells

Following transfection, transiently transfected SCC13y cells were serially passaged onto a 100 mm² tissue culture dish. After 1 week of expansion, these cells were again passage onto a 150 mm² tissue culture dish and allowed to grow for an additional week. This allows expansion of stable transfectants, as well as loss of GFP expression in the transient transfectants. Cells were removed using 0.5 mM EDTA and 0.1% trypsin. After centrifugation (440×g for 5 minutes), cells were resuspended in serum-containing medium at a density of $5\times10^6$ cells/ml with 5 mg/ml PI. This suspension was then filtered through 42 µm sterile mesh (Tetko, Inc.) immediately prior to sorting. Transfected SCC13y cells were sorted on a FACStar Plus (Becton Dickinson) equipped with a coherent argon 488 nm laser. Cells were sorted at a rate of 2000/second and samples were collected post-sort to check viability and GFP expression. Non-viable cells were not collected.

Immediately following cell sorting, SCC13y$^{GFP+}$ cells were reinitiated into culture. All cells obtained (typically $1-3\times10^4$) were plated onto 100 mm² dishes with mitomycin C-treated Swiss mouse 3T3 fibroblast feeder layers. Cells were monitored every other day using an IX-70 inverted fluorescent microscope (Olympus) with a GFP short band pass filter. Non-GFP expressing colonies were removed by scraping colonies from the dish. Stable GFP expressing colonies were refed and allowed to expand. When GFP expressing colonies had grown to an estimated density of 1000 cells or more, cells were replated onto 100 mm² plates with mitomycin C treated 3T3 feeder layers and expanded. Baseline percentage of SCC13y$^{GFP+}$ cells in the population was established by flow cytometry as described above.

Stability of SCC13y$^{GFP+}$ with Serial Cultivation

SCC13y$^{GFP+}$ cells were grown in standard SCC media under the following conditions. All cells were grown in triplicate in 3 wells of a 6 well plate with mitomycin C inactivated 3T3 feeder layers. Every 6th day, each culture was harvested with 0.1% trypsin and $1\times10^5$ cells passed into a new well of a 6 well plate with feeder layers. Media was changed twice weekly. At 4 week intervals, samples were suspended at $2\times10^6$ cells/ml and analyzed for GFP expression by flow cytometry as described above.

In Vitro Growth of SCC13y$^{GFP+}$

Growth profiles were determined by plating $1\times10^5$ cells into replicate wells of 6-well tissue culture plates without mitomycin C treated mouse 3T3 feeder layers. Replicate wells for each sample were harvested daily and total cell number determined by hemacytometer counting. Mean cell numbers are tested for differences between SCC13y control (non-transfected) and SCC13y$^{GFP+}$ using standard ANOVA statistical analysis.

Growth of SCC13y$^{GFP+}$ Cells in Athymic Mice

The capacity of GFP expressing SCC13y cells to grow as tumor xenografts was determined by injection of $5$–$10\times10^6$ cells/100 µl of unsupplemented DME into athymic, nude (nu/nu), 3–4 week old, female mice (Harlan-Sprague-Dawley). Each animal was inoculated with 1 dorsal and 1 ventral subcutaneous injection each of untransfected SCC13y and SCC13y$^{GFP+}$, respectively. The cell type injected at each location was switched in alternate mice. A total of 8 mice with 1 test of each cell line each was examined. All mice were housed in accredited animal research facilities and experimental techniques and protocols have been reviewed and approved by the Health Sciences Animal Care Committee of the University of Wisconsin-Madison.

Clonogenic Survival of SCC13y$^{GFP+}$

Colony forming efficiency (CFE) was determined by plating a range of cell densities from exponentially growing cultures into replicate 6-well plates containing mitomycin C treated mouse 3T3 feeder layers. After approximately two weeks of growth in standard SCC plates were fixed for 10 minutes in 10% formalin, rinsed with tap water, and stained overnight with methylene blue. Colonies of ~50 cells were counted. CFE was calculated as [(number colonies counted)/(number of cells seeded)]×100%. Mean CFE was determined for replicates and tested for differences between non-transfected SCC-13y control and SCC13y$^{GFP+}$ using standard ANOVA statistical analysis Radiation Survival of SCC13y$^{GFP+}$ Radiation survival for the SCC13y and SCC13y$^{GFP+}$ cells was determined by irradiating replicate exponentially growing cultures with 0, 1, 3, 6, and 10 Gy doses. Cultures were maintained in a 25 mm$^2$ tissue culture flask and had a total cell number of $1$–$2\times10^6$ cells per flask when irradiated with a $^{137}$Cs hot box with current dose rate of 5.86Gy/min. Following irradiation, cells were trypsinized, counted, diluted, and plated in 3–5 60 mm$^2$ dishes on mitomycin C treated 3T3 feeder layers over a range of cell densities to allow detection of colony growth. Colony forming efficiency was determined as described above. Mean CFE was determined for replicates and tested for differences between non-transfected SCC13y and SCC13y$^{GFP+}$ using standard ANOVA statistical analysis.

Histological Analysis of Transfected Organotypic Cultures

SCC13y$^{GFP+}$ cells at 9(passage were plated at a density of 500, 5000, 100,000 cells/collagen base and grown in organotypic co-culture for 16 days. Organotypic cultures were fixed overnight in 4% paraformaldehyde before embedding in paraffin. Sections (5 µm) were cut and alternate sections were mounted and stained with hemotoxylin and eosin (H&E) by Surgical Pathology, UW-Madison Hospital, Madison, Wis. Non-H&E sections were rehydrated, stained with 5 mg/ml Hoechst dye (33258) for 15 minutes, dehydrated and mounted using Cytoseal mounting media (Stephens Scientific). Sections were viewed using an IX-70 inverted fluorescent microscope (Olympus) equipped with a dual FITC-Hoechst filter (470 nm±20 and 525 nm±band pass).

Analysis of GFP Expression by Confocal Microscopy

GFP-expressing SCC13y cells at 9(passage were plated at a density of 500 cells/collagen raft and grown in organotypic culture for 16 days as described above. Organotypic cultures were fixed overnight in 4% paraformaldehyde-PBS and rinsed for >1 hr in a 0.1 M glycine-PBS solution at 4° C. Cultures were mounted, coverslipped using Vectashield mounting media (Vector labs) and sealed with rubber cement. GFP expression was analyzed using a confocal laser scanning microscope (Nikon Diaphot 200) with an excitation wavelength of 488 nm and detection with a 500–530 nm bandpass filter. Images were taken at approximately 1 µm intervals starting at the upper cornified layer (W. M. Keck Neural Imaging Laboratory, University of Wisconsin-Madison).

B. Results

Efficiency of Transfection of SCC13y

One objective of this set of experiments was to optimize the transfection efficiency of SCC13y. Transient transfection is defined as positive expression of the transfected construct occurring within 48 hours following transfection. There were predominantly three variables which were examined for an effect on transfection efficiency: concentration of DNA, concentration of GeneFECTOR, and cell density. Table 7 in Appendix 1 summarizes the observed percentage of GFP cells following transfection as determined by flow cytometry. The optimal SCC13y transfection efficiency of 21.4% was observed with 10 µg of input DNA using a 1:2 ratio of DNA:GeneFECTOR. Optimal cell density for transfection was observed when cells were in exponential growth phase, but before the cultures reached confluence. Although nonviable cells may be positive transfectants, these cells were excluded from analysis by gating out this population with the flow cytometry software. In all experiments, the total number of dead cells observed was small relative to the total number of cells analyzed (<8%).

Isolation of SCC13y$^{GFP+}$ Populations

Using the optimal transient transfection conditions described above, exponentially growing SCC13y were transfected with the pGreenLantern GFP plasmid and stable SCC13y$^{GFP+}$ cells were isolated. Stable transfection is defined as positive GFP expression for a period of no less than 4 weeks of serial cultivation. GFP expression of transiently transfected cells varied over a range of approximately 2 logs on the flow cytometry histogram and represented approximately 4% of the total population of transfected cells. Following plating of sorted cells, individual SCC13y$^{GFP+}$ colonies were observed to have variable levels of expression within (and between) colonies, however, mixed GFP$^+$/GFP$^-$ colonies were rarely observed. By the third passage, a post-sort check following sorting of the SCC13y$^{GFP+}$ population showed that approximately 85% of the cells expressed GFP.

Stable GFP Expression in SCC13y$^{GFP+}$ Transfectants

Pooled populations of SCC13y$^{GFP+}$ at passage 7, exhibit a baseline level of GFP expression approximately 1 log greater than the autofluorescent background detected in non-GFP expressing SCC13y The percentage of SCC13y$^{GFP+}$ cells in the population was found to be 90% using FACS analysis software. This compares well with the percentage of GFP$^{30}$ cells found after sorting in earlier passages discussed above (85%). SCC13y$^{GFP+}$ cells were defined as all events with a GFP signal greater than the highest GFP signal detected in viable, non-transfected SCC13y cells. Visual observation using fluorescent microscopy confirm that few, if any, non-GFP-expressing SCC13y present in this population.

Another set of experiments has demonstrated that GFP expression in SCC13y is stable over longer periods of time. Histograms of GFP expression determined 12 passages following isolation of stable SCC13y$^{GFP+}$ demonstrate little change in the percentage of GFP$^{30}$ (85%), and GFP signal remains approximately 1 log greater than non-GFP expressing controls. Fluorescent microscopy confirmed that visually, 100% of the cells appear green.

In Vitro SCC13y Growth is Unaffected by GFP Expression

In vitro growth of SCC13y$^{GFP+}$ cells was next examined to determine if GFP expression affected SCC13y growth. SCC13y$^{GFP+}$ and non-transfected SCC13y cells grew at nearly identical growth rates and achieved similar total cell numbers after 6 days of in vitro growth. In addition, both cell lines demonstrated a typical initial lag phase of slow growth followed by an exponential, rapidly growing phase.

SCC13y$^{GFP+}$ Remain Tumorigenic

The SCC13y cell line is malignant and forms tumors in nude mice. SCC13y$^{GFP+}$ cells were examined to determine if exogenous GFP expression alters the ability of SCC13y cells to form tumor xenografts. Of the 8 mice injected with both cell lines, every mouse has produced an observable tumor within the first week following injection. In addition, there have not been any tumors which have regressed (monitored up to 8 weeks). These experiments continue with all tumors increasing in size on a weekly basis, although, each tumor is not necessarily growing at the same rate.

Unaltered Radiation Response of SCC13y$^{GFP+}$

The radiation response of the SCC13y cell line has been well characterized (Petereit, D. G., et al., 1994). A radiation dose of 6 Gy kills approximately 99% (2 logs) and 10 Gy kills approximately 99.9% (3 logs) of exponentially growing cells. Similar experiments with GFP expressing SCC13y cells over the same dose range produced nearly identical results. Also, the morphology of the SCC13y$^{GFP+}$ colonies assayed in this clonogenic survival assay appear to be similar to the non-transfected SCC13y cells. Colonies did not demonstrate any differences in colony size or cell density over the 2 week assay period. These observations confirm a lack of effect of GFP expression on SCC13y radiation sensitivity.

Co-culture of SCC13y Does Not Alter Normal Stratification of BC-1-Ep/SL Keratinocytes The BC-1-Ep/SL cells have been previously shown to form fully differentiated skin in organotypic culture[7]. Introduction of a malignant cell type into this functionally normal tissue does not appear to alter the capacity of the BC-1-Ep/SL to exhibit normal squamous differentiation. Observations of growing co-cultures of BC-1-Ep/SL and SCC13y$^{GFP+}$ cells identify a multilayered sheet that is similar to stratified epithelium. The BC-1-Ep/SL cells continue to exhibit several characteristics of normally differentiating epidermis. Basal cells are observed to form a single layer of cuboidal cells resting at the junction of the epidermis and the dermal equivalent. The rounded morphology and high nuclear to cytoplasmic ratio indicates an actively dividing population of keratinocytes. Normal differentiation is evident in cells moving toward the skin surface as they flatten and become squamous and loose the nucleus in the upper layers of the tissue.

Identification of 3-D Tumor Foci in Organotypic Culture SCC13y$^{GFP+}$ and BC-1-Ep/SL Stratifying Epithelia To determine if the malignant SCC13y$^{GFP+}$ cell line was able to form tumor foci in a predominantly non-malignant keratinocyte culture, varying numbers of SCC13y$^{GFP+}$ cells were seeded onto an organotypic BC-1-Ep/SL keratinocyte culture. SCC13y$^{GFP+}$ cells were plated at 500, 5000, and 100,000 cells per 300,000 BC-1-Ep/SL cells at the start of the experiment. After two weeks in culture, all experimental groups formed growing tumor foci of GFP$^+$ cells. The highest conentration of SCC13y$^{GFP+}$ cells (100,000 SCC13y$^{GFP+}$ to 300,000 BC-1-Ep/SL cells) produced a continuous sheet of GFP$^{30}$ cells which appeared to overwhelm growth of the BC-1-Ep/SL cells. Confocal microscopy which allows examination of organotypic cultures in three dimensions confirmed the formation of a number of individual SCC13y$^{GFP+}$ tumor foci growing within the normal tissue-like structure formed by the organotypic culture of BC-1-Ep/SL cells. The SCC13y$^{GFP+}$ foci grew predominantly in spheroid-shaped masses and contained no less than 50 cells per focus. Interestingly, it appeared that the SCC13y$^{GFP+}$ cell foci grew uninterrupted by BC-1-Ep/SL (non-green) co-cultured cells, i.e., all GFP cells of a foci were adjacent to each other. These observations confirm that SCC13y malignant cells can be co-cultured within an engineered human tissue and that GFP expression is an efficient labelling method which can be used to identify and visualize even very small human tumor foci.

REFERENCES

1. Allen-Hoffmann, B. L. and J. G. Rheinwald, "Polycyclic aromatic hydrocarbon mutagenesis of human epidermal keratinocytes in culture," *PNAS USA* 81:7802–7806, 1984.
2. Allen-Hoffmann, B. L. and S. Schlosser, "Normal Growth and Differentiation in a Spontaneously Immortalized Near-Diploid Human Keratinocyte Cell Line, BC-1-Ep/SL, 1998.
3. Breitkruetz, D., et a., "Integrin and basement membrane normalization in mouse grafts of human keratinocytes—implications for epidermal homeostasis," *Differentiation* 61(3):195–209, 1997.
4. Choate, K. A., et al., "Corrective gene transfer in the human skin disorder lamellar ichthyosis," *Nature Medicine* 2(11):1263–1267, 1996.
5. Choate, K. A. and P. A. Khavari, "Sustainability of keratinocyte gene transfer and cell survival in vivo," *Human Gene Therapy* 8:895–901, 1997.
6. Drosdoff, V. and W. J. Pledger, *J. Cell. Biol.* 123:909–919, 1993.
7. Fenjves, E. S., et al., "Systemic delivery of secreted protein by grafts of epidermal keratinocytes: Prospects for keratinocyte gene therapy," *Human Gene Therapy* 5:1241–1248, 1994.
8. Fenves, E. S., "Approaches to gene transfer in keratinocytes," *J. Invest. Dermatol.* 103(5):70S-75S.
9. Fort, P., et al., *Nucl. Acids Res.* 13:1431–1442, 1985.
10. Garlick, J. A., et al., "Retrovirus-mediated transduction of cultured epidermal keratinocytes," *J. Invest. Dermatol.* 97:824–829, 1991.
11. Gerrard, A. J., et al., "Towards gene therapy for haemophilia B using primary human keratinocytes, *Nature Genetics* 3:180–183, 1993.
12. Green, H., *Cell* 11:405–416, 1977.
13. Greenhalgh, D. A., et al., "Epidermis: An attractive target tissue for gene therapy," *J. Invest. Dermatol.* 103S:63S–69S, 1994.

14. Haddow, A., "Molecular repair, Wound healing and carcinogenesis: tumor production a possible overhealing?", *Adv. Cancer Res.* 16:181–234, 1972.

15. Hall, E. J., "Time, Dose, and Fractionation in Radiotherapy," In Radiobiology for the Radiologist (Third Edition), pp. 239–260, Philadelphia: J. B. Lippincott Company, 1988.

16. Hines, M. D., et al., "Keratinocyte growth factor inhibits cornified envelope formation and nucleosomal fragmentation in cultured human keratinocytes," *J. Biol. Chem.* 271:6245–6251, 1996.

17. Javaherian, A., et al., "Normal keratinocytes suppress early stages of neoplastic progression in stratified epithelium," *Cancer Res.* 58:2200–2208, 1998.

18. Kudlow, J. E., e al., "Transforming growth factor-α in the mammalian brain," *J. Biol. Chem.* 264:3880–3883, 1989.

19. Leigh, I. M. and F. M. Watt, "The culture of human epidermal keratinocytes," In (Edited by Leigh, I. M., B. Lane, F. M. Watt) *The Keratinocyte Handbook*, Cambridge University Press (Cambridge, Great Britain), 1994.

20. Miyamoto, C., et al., *Proc. Natl. Acad. Sci. USA* 82:7232–7236, 1985.

21. Parenteau, N., "Skin Equivalents," In *Keratinocyte Methods*, 1994.

22. Petereit, D. G., et al., "Combining polyamine depletion with radiation therapy for rapidly dividing head and neck tumors: strategies for improved locoregional control," *Int. J. Radiation Oncology Biol. Phys.* 28:891–898, 1994.

23. Petereit, D. G., et al., "The adverse effect of treatment prolongation in cervical carcinoma," *Int. J. Rad. Biol. Phys.* 32:1301–1307, 1995.

24. Pietenpol, J. A., et al., *Proc. Natl. Acad. Sci. USA* 87:3758–3762, 1990.

25. Rheinwald, J. G., et al., "Tumorigenic keratinocyte lines requiring anchorage and fibroblast support cultured from human squamous cell carcinoma," *Cancer Res.* 41:1657–1663, 1981.

26. Sachsenmeier, K. F., et al., "Transforming growth factor β1 inhibits nucleosomal fragmentation in human keratinocytes following loss of adhesion," *J. Biol. Chem.* 271:5–8, 1996.

27. Sadek, C. M. and B. L. Allen-Hoffmann, "Cytochrome P450IA1 is rapidly induced in normal human keratinocytes in the absence of xenobiotics: A novel suspension-mediated mechanism for CYPIA1 expression," *J. Biol. Chem.* 269:16067–16074, 1994.

28. Sharples, K., et *DNA* 6:239–244, 1987.

29. Vogel, J., "Keratinocyte gene therapy," *Arch. Dermatol.* 129(11):1478–1483, 1993.

30. Xu, Y., et al., "Human epidermal growth factor receptor cDNA is homologous to a variety of RNAs overproduced in A431 carcinoma cells," *Nature* 309:806–810, 1984.

Appendix I

TABLE 1

Chromosomal aberrations with passage
Chromosomal analysis was done on 20 spreads of the parental
BC-1-Ep at passage 3 and the BC-1-Ep/SL cells at passages 31 and 54.

| Passage # | Spreads | 46, XY | 47, XY + i(8q) | 48, XY + i(1q) + i(8q) | 48, XY + i(8q) + mar | 49, XY + i(1q) + i(8q) + mar |
|---|---|---|---|---|---|---|
| 3 | 20 | 20 | 0 | 0 | 0 | 0 |
| 31 | 20 | 0 | 20 | 0 | 0 | 0 |
| 54 | 20 | 0 | 17 | 1 | 1 | 1 |

TABLE 2

Tumorigenicity of BC-1-Ep/SL cells in nude mice
To determine if BC-1-Ep/SL cells formed tumors, cells were injected
subcutaneously into the flanks of six nude mice at $5 \times 10^6$
cells/100 μl F12. For a negative control. BC-1-Ep 6°
were injected into the flanks of six nude mice at $3 \times ^6$
cells/100 μl F12. For a positive control. SCC4y 20°
were injected into flanks of four nude mice. Mice were weighted and
tumors measured 26 days later. The injection strategy is shown below.

| Animal # | Condition | Body Weight (gm) | Area of tumor (mm³) |
|---|---|---|---|
| 1 | left flank = BC-1-Ep 6° | 22 | — |
|  | right = BC-1-Ep/SL 35° |  | — |
| 2 | left = BC-1-Ep 6° | 24 | — |
|  | right =BC-1-Ep/SL 35° |  | — |
| 3 | left =SCC4y 20° | 21 | 105.2 |
|  | right = BC-1-Ep/SL 35° |  | — |
| 4 | left = BC-1-Ep 6° | 25 | — |
|  | right =SCC4y 20° |  | 1183.6 |
| 5 | left flank =BC-1-Ep 6° | 23 | — |
|  | right = BC-1-Ep/SL 35° |  | — |
| 6 | left = Bc-1-Ep 6° | 22 | — |
|  | right = BC-1-Ep/SL 35° |  | — |
| 7 | left = SCC4y 20° | 22 | 51.3 |
|  | right = BC-1-Ep/SL 35° |  | — |
| 8 | left =BC-1-Ep 6° | 19 | — |
|  | right = SCC4y 20° |  | 463.3 |

TABLE 3

Formation of cornified envelopes in BC-1-Ep/SL cells
BC-1-Ep/SL cells were grown in the presence of a 3T3
feeder layer. Feeders were removed and 2–3* days later, cells
were suspended for 24 hours at $-10^6$/ml in 3F12:1DME +
penicillin/streptomycin made semisolid with 1.68%
methylcellulose. Adherent cells were rinsed and incubated 24
hours in 3F12:1DME + penicillin/streptomycin. Envelopes
were isolated by boiling the cells for 5 minutes in PBS
containing 1% SDS and 20 mM DTT, and counted
using a hemacytometer.

|  | Treatment | Adherent | Suspended |
|---|---|---|---|
| Exp. 1 | Parent (*4°) | 1.51% | 43.3% |
|  | BC-1-Ep/SL (31°) | 1.32% | 69.8% |
| Exp. 2 | Parent (6°) | 1.79% | 32.8 |
|  | BC-1-Ep/SL (33°) | 1.05% | 73.7% |

TABLE 4

DNA Concentration Imports on Transient Transfection
Efficiency in BC-1-Ep/SL Cells
BC1-Ep/SL cells were transfected with the GFP containing plasmid
pGreenLantern (Gibco) and pcDNA3neo(Invitrogen) with the various
anounts of DNA depicted below. The ratio of DNA to GeneFECTOR
was kept constant at 1:4. Transfection efficiency was obtained
using FACS. Cell number was determined by trypsinization and
counting of keratinocytes using a hemacytometer.

| DNA concentration | Aug. 26, 1997 % GFP + Cells | Dec. 16, 1997 % GFP + Cells | Dec. 22, 1997 % GFP + Cells |
|---|---|---|---|
| 15 µg pGL + 5 µg pcDNA3 | 3.79% | 13.64% | 9.88% |
| 20 µg pGL + 6.7 µg pcDNA3 | 3.2% | 5.25% | 8.85% |
| 25 µg pGL + 8.3 µg pcDNA3 | 1.98% | 12.49% | 3.33% |
| Cell Confluence | 70% | 35.40% | 35.40% |

TABLE 5

Ratio of DNA to GeneFECTOR Affects
Transient Transfection Efficiency
BC-1-Ep/SL cells were transfected with varying ratios of plasmid DNA
(pGL + pcDNA3neo) to transfection reagent (GeneFECTOR). The
DNA concentration was held constant at 15 µg of pGreenLantern
and 5 µg of pcDNA3neo. Transfection efficiency was obtained
using FACS. Cell number was determined by cell
trypsinization and hemacytometer counting.

| Ratio of DNA to Genefector | Jan. 30, 1998 % GFP + Cells | Feb. 20, 1998 % GFP + Cells | Feb. 20, 1998 % GFP + Cells |
|---|---|---|---|
| 1:2 | 4.74% | 15.2% | 6.94% |
| 1:3 | 7.23% | 17.54% | 19.36% |
| 1:4 | 3.3% | 7.95% | 16.99% |
| Cell Confluence | 50% | 30% | 30% |

TABLE 6

Stable Transfection of BC-1-Ep/SL. Cells Using pGreenLantern
BC1-Ep/SL cells were tranfected with pGreenLantern and pcDNA3
using optimal transient transfection parameters. Twenty-four hours
post-transfection, keratinocytes were suspended at a density of
4–6 × 10$^6$/ml and stained with 5 mg/ml propidium iodide.
BC-1-Ep/SL cells were sterile sorted into four categories based on the
fluorescent intensity of GFP. Colony forming efficiency was calculated
by counting the number of colonies formed from one thousand cells
plated per p60. GFP positive colonies were counted using an
inverted fluorescent microscope with a GFP short pass filter.
This table represents one cell sorting experiment.

| Fluorescent Intensity of GFP | Events Sorted | Colony Forming Efficiency | Total Colonies Formed | GFP + Colonies | % GFP + Colony Formers |
|---|---|---|---|---|---|
| Brightest | 63,375 | 0.13% | 83 | 0 | 0% |
| Brights | 54,802 | 0.38% | 208 | 4 | 1.9% |
| Dims | 37,161 | 0.86% | 319 | 6 | 1.9% |
| Dimmest | 62,432 | 0.34% | 212 | 2 | 0.9% |
| | | | | Total | 4.7% |

TABLE 7

| | % Transfection | | | |
|---|---|---|---|---|
| | Percent of Confluency of Dish | | | |
| [GeneFector] | 60% | 75% | 100% | [DNA] |
| 1 µg | 1.6 | 1.9 | 1.4 | 1 µg |
| 2 µg | 4.6 | 4.4 | 2.7 | 1 µg |
| 10 µg | 9.9 | 9.7 | 8.0 | 10 µg |
| 20 µg | 10.4 | 21.4 | 13.3 | 10 µg |

We claim:

1. A method for screening compounds comprising:
   1) providing:
      a) a culture comprising a human keratinocyte cell line, wherein said cell line i) is immortalized; ii) is nontumorigenic; iii) forms cornified envelopes when induced to differentiate; iv) undergoes normal squamous differentiation in organotypic culture; and v) maintains cell type-specific growth requirements and wherein the cell line originated with ATCC CRL 12191; and
      b) a test compound;
   2) treating said host cells with said one or more test compounds; and
   3) monitoring said culture.

2. The method of claim 1, wherein said culture is an organotypic culture.

3. The method of claim 2, wherein said culture is a monolayer culture.

4. The method of claim 1, wherein said cell type-specific growth requirements include requirements selected from the group consisting of 1) exhibition of morphological characteristics of normal human keratinocytes when cultured in standard keratinocyte growth medium in the presence of mitomycin C-treated 3T3 feeder cells; 2) dependence on epidermal growth factor for growth; and 3) inhibition of growth by transforming growth factor β1.

5. The method of claim 1, wherein said cell line comprises an exogenous gene.

6. The method of claim 5, wherein said exogenous gene is green fluorescent protein.

7. The method of claim 1, wherein said compounds are selected from the group consisting of cytostatic compounds, therapeutic compounds, and cosmetic compounds.

8. The method of claim 1, wherein said culture comprises ATCC CRL-12191 cells.

9. A method for screening compounds comprising:
   1) providing:
      a) a culture comprising a human keratinocyte cell line, wherein the cell line originated with ATCC CRL 12191 wherein said cell line i) is immortalized; ii) is nontumorigenic; iii) forms cornified envelopes when induced to differentiate; iv) undergoes normal squamous differentiation in organotypic culture; and v) maintains cell type-specific growth requirements, wherein said cell type-specific growth requirements include requirements selected from the group consisting of 1) exhibition of morphological characteristics of normal human keratinocytes when cultured in standard keratinocyte growth medium in the presence of mitomycin C-treated 3T3 feeder cells; 2) dependence on epidermal growth factor for growth; and 3) inhibition of growth by transforming growth factor β1; and b) a test compound;

2) treating said host cells with said one or more test compounds; and 3) monitoring said culture.

10. The method of claim 9, wherein said culture is an organotypic culture.

11. The method of claim 9, wherein said culture is a monolayer culture.

12. The method of claim 9, wherein said cell line comprises an exogenous gene.

13. The method of claim 12, wherein said exogenous gene is green fluorescent protein.

14. The method of claim 9, wherein said compounds are selected from the group consisting of cytostatic compounds, therapeutic compounds, and cosmetic compounds.

15. The method of claim 9, wherein said culture comprises ATCC CRL-12191 cells.

16. A method for screening compounds comprising:

1) providing:
   a) a culture comprising a human keratinocyte cell line, wherein the cell line originated with ATCC CRL 12191, wherein said cell line i) is immortalized; ii) is nontumorigenic; iii) forms cornified envelopes when induced to differentiate; iv) undergoes normal squamous differentiation in organotypic culture; and v) maintains cell type-specific growth requirements, wherein said cell type-specific growth requirements include requirements selected from the group consisting of exhibition of morphological characteristics of normal human keratinocytes when cultured in standard keratinocyte growth medium in the presence of mitomycin C-treated 3T3 feeder cells; dependence on epidermal growth factor for growth; and inhibition of growth by transforming growth factor $\beta 1$; and vi) and comprises an exogenous gene; and
   b) a test compound;

2) treating said host cells with said one or more test compounds; and 3) monitoring said culture.

17. The method of claim 16, wherein said culture is an organotypic culture.

18. The method of claim 16, wherein said culture is a monolayer culture.

19. The method of claim 18, wherein said exogenous gene is green fluorescent protein.

20. The method of claim 16, wherein said compounds are selected from the group consisting of cytostatic compounds, therapeutic compounds, and cosmetic compounds.

21. The method of claim 16, wherein said culture comprises ATCC CRL-12191 cells.

* * * * *

UNITED STATES PATENT AND TRADEMARK OFFICE
CERTIFICATE OF CORRECTION

PATENT NO. : 6,884,595 B2
DATED : April 26, 2005
INVENTOR(S) : B. Lynn Allen-Hoffmann et al.

It is certified that error appears in the above-identified patent and that said Letters Patent is hereby corrected as shown below:

Column 1,
Line 60, "manor" should be -- major --.

Column 3,
Line 65, "ant" should be -- and --.

Column 6,
Line 20, "an" should be -- in --.
Line 44, "EP" should be -- Ep --.

Column 7,
Line 57, "... 0.66 mM calcium," should be -- ... 0.66 mM calcium) --.

Column 8,
Line 34, "infected" should be -- injected --.

Column 9,
Line 3, "[32p]" should be -- [32P] --.

Column 10,
Line 18, "a:" should be -- at --.

Column 11,
Line 58, "positive PC-1" should be -- positive BC-1 --.

Column 14,
Line 65, "removes" should be -- removed --.

Column 16,
Line 62, "use" should be -- used --.

Column 18,
Line 31, -- methods -- should be inserted between "standard" and "for"

Column 19,
Line 33, "FP" should be deleted

UNITED STATES PATENT AND TRADEMARK OFFICE
CERTIFICATE OF CORRECTION

PATENT NO. : 6,884,595 B2
DATED : April 26, 2005
INVENTOR(S) : B. Lynn Allen-Hoffmann et al.

It is certified that error appears in the above-identified patent and that said Letters Patent is hereby corrected as shown below:

Column 23,
Line 1, "GFP30" should be deleted
Line 12, "GFP30" should be deleted
Line 49, "SCC13y" should be -- SCC13yGFP+ --.

Column 24,
Line 13, "GFP30" should be deleted
Line 54, "Fenves" should be -- Fenjves --.

Column 25,
Line 60, "et." should be -- et al. --.

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,884,595 B2
DATED : April 26, 2005
INVENTOR(S) : Allen-Hoffmann et al.

It is certified that error appears in the above-identified patent and that said Letters Patent is hereby corrected as shown below:

Column 1,
Lines 13-16, should read -- This invention was made with United States government support awarded by the following agency: NIH Grant No. AR40284; CA66786; and AR42853. The United States has certain rights in this invention. --.

Signed and Sealed this

Twenty-fifth Day of April, 2006

JON W. DUDAS
*Director of the United States Patent and Trademark Office*